United States Patent
Zhu et al.

(10) Patent No.: US 12,006,291 B2
(45) Date of Patent: Jun. 11, 2024

(54) PROCESSES FOR THE PREPARATION OF 4,6,7-TRIFLUORO-1H-INDOLE-2-CARBOXYLIC ACID

(71) Applicant: ENANTA PHARMACEUTICALS, INC., Watertown, MA (US)

(72) Inventors: Kaicheng Zhu, Belmont, MA (US); Tao Wang, Berkeley Heights, NJ (US); Jiajun Zhang, Cambridge, MA (US); Hui Cao, Belmont, MA (US); Ruichao Shen, Belmont, MA (US); Guoqiang Wang, Belmont, MA (US); George G. Wu, Waltham, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 18/095,155

(22) Filed: Jan. 10, 2023

(65) Prior Publication Data

US 2023/0234922 A1    Jul. 27, 2023

Related U.S. Application Data

(60) Provisional application No. 63/307,950, filed on Feb. 8, 2022, provisional application No. 63/298,471, filed on Jan. 11, 2022.

(51) Int. Cl.
C07D 209/42    (2006.01)

(52) U.S. Cl.
CPC ............... C07D 209/42 (2013.01)

(58) Field of Classification Search
CPC ................................... C07D 209/42
See application file for complete search history.

(56) References Cited

U.S. PATENT DOCUMENTS

| | | |
|---|---|---|
| 11,319,325 B1 | 5/2022 | Zhang et al. |
| 11,325,916 B1 | 5/2022 | Shen et al. |
| 11,339,170 B1 | 5/2022 | Gao et al. |
| 11,352,363 B1 | 6/2022 | Wang et al. |
| 11,358,953 B2 | 6/2022 | Panarese et al. |
| 11,384,090 B2 | 7/2022 | Wang et al. |
| 2018/0099981 A1 | 4/2018 | Estrada et al. |
| 2019/0161472 A1 | 5/2019 | Ombrato et al. |
| 2022/0033383 A1 | 2/2022 | Panarese et al. |
| 2022/0041652 A1 | 2/2022 | Panarese et al. |
| 2022/0048944 A1 | 2/2022 | Panarese et al. |
| 2022/0162216 A1 | 5/2022 | Wang et al. |
| 2022/0162231 A1 | 5/2022 | Wang et al. |
| 2022/0380377 A1 | 12/2022 | Zhang et al. |
| 2022/0402926 A1 | 12/2022 | Zhang et al. |
| 2023/0103494 A1 | 4/2023 | Wang et al. |
| 2023/0115107 A1 | 4/2023 | Gao et al. |
| 2023/0122228 A1 | 4/2023 | Shen et al. |
| 2023/0151019 A1 | 5/2023 | Cao et al. |
| 2023/0159545 A1 | 5/2023 | Panarese et al. |
| 2023/0159546 A1 | 5/2023 | Kass et al. |
| 2023/0174531 A1 | 6/2023 | Panarese et al. |
| 2023/0203048 A1 | 6/2023 | Wang et al. |
| 2023/0295175 A1 | 9/2023 | Zhu et al. |

FOREIGN PATENT DOCUMENTS

| | | | |
|---|---|---|---|
| WO | 2019086141 A1 | 5/2019 | |
| WO | 2019086142 A1 | 5/2019 | |
| WO | WO-2019086142 A1 * | 5/2019 | ........... A61K 31/437 |
| WO | 2020081636 A1 | 4/2020 | |
| WO | 2020221826 A1 | 11/2020 | |
| WO | 2021252644 A1 | 12/2021 | |
| WO | 2022013684 A1 | 1/2022 | |
| WO | 2022020242 A1 | 1/2022 | |
| WO | 2022020711 A1 | 1/2022 | |
| WO | 2022109363 A1 | 5/2022 | |
| WO | 2023086350 A1 | 5/2023 | |

* cited by examiner

*Primary Examiner* — Kamal A Saeed
(74) *Attorney, Agent, or Firm* — Edgar W. Harlan; Carolyn S. Elmore; Elmore Patent Law Group, P.C.

(57) ABSTRACT

The present invention relates to processes for preparing a Compound (1):

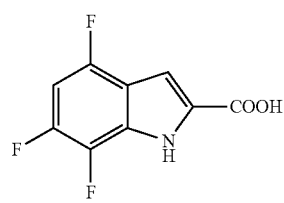

(1)

or a pharmaceutically acceptable salt or solvate thereof. Compound (1) is useful as in many pharmaceutical agents, especially is useful as key intermediate in the synthesis of certain SARS-CoV-2 3CLpro inhibitors.

7 Claims, No Drawings

PROCESSES FOR THE PREPARATION OF 4,6,7-TRIFLUORO-1H-INDOLE-2-CARBOXYLIC ACID

RELATED APPLICATIONS

This application claims the benefit of U.S. Provisional Application No. 63/298,471, filed on Jan. 11, 2022, and U.S. Provisional Application No. 63/307,950, filed on Feb. 8, 2022. The entire teachings of the above applications are incorporated herein by reference.

TECHNICAL FIELD

The present invention relates generally to the processes and intermediates useful in the preparation 4,6,7-trifluoro-1H-indole-2-carboxylic acid which is an intermediate in the synthesis of certain SARS-CoV-2 3CLpro inhibitors.

BACKGROUND OF THE INVENTION

Coronaviruses are enveloped, positive-sense, single-stranded RNA viruses. The genomic RNA of CoVs has a 5'-cap structure and 3'-poly-A tail and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO 2004/101742 A2, US 2005/0143320 A1, US 2006/0014821 A1, US 2009/0137818 A1, WO 2013/049382 A2, WO 2013/166319 A1, WO 2018/042343, WO 2018/023054, WO2005113580, and WO 2006/061714).

The indole ring system is one of the most ubiquitous heterocycles in nature. Because of the great structural diversity of biologically active indoles, the indole ring system has become an important structural component in many pharmaceutical agents. For over several decades, the synthesis and functionalization of indoles has been a major area of focus for synthetic organic chemists, and numerous methods for the preparation of indoles have been developed. Key considerations, including starting material availability, functional group tolerance and specific substitution patterns, often determine which particular indole synthetic method will be utilized. The process chemist is mainly interested in mild synthetic methods that provide rapid assembly of the indole ring, tolerate a wide range of functional groups, and are atom economical. The implementation of practical, safe, and scalable methods for the large-scale preparation of indoles is of critical interest to who design industrial or manufacturing syntheses, as well as researchers in academia.

Substituted 1H-indole-2-carboxylic acids can be synthesized by the Hemetsberger approach using an azide intermediate (Refer to WO2019086142 and WO2020221826). However, in a large-scale process, using an azide intermediate is challenging due to safety concerns. There is a need for an efficient process for the preparation of 4,6,7-trifluoro-1H-indole-2-carboxylic acid that does not proceed via an azide intermediate.

SUMMARY OF THE INVENTION

The present invention provides methods for preparing 4,6,7-trifluoro-1H-indole-2-carboxylic acid, Compound (1):

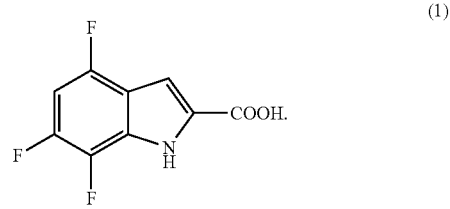

The invention further relates to methods for increasing product yield and improving the scalability for large scale production of Compound (1).

Compound (1) is a starting material for certain biologically active compounds, such as compounds which are inhibitors of the coronavirus 3CLpro. See, for example, U.S. Pat. Nos. 11,325,916; 11,319,325, and WO 2022/109363, each of which is incorporated herein by reference in its entirety.

DETAILED DESCRIPTION OF THE INVENTION

In one embodiment, the present invention provides a process for the preparation of Compound (1),

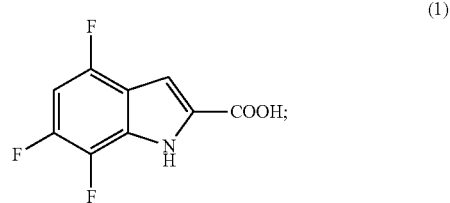 [SMILES: O=C(O)c1cc2c(F)cc(F)c(F)c2[nH]1]

the process comprising the steps of:
(i) reacting Compound (a), 2,4,5-trifluorobenzoic acid, with a bromination agent, to produce Compound (b):

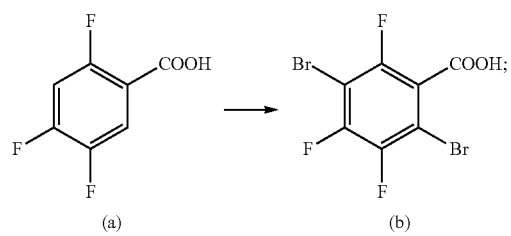 [SMILES: O=C(O)c1cc(F)c(F)cc1F ; O=C(O)c1c(F)c(Br)c(F)c(F)c1Br]

(ii) reacting Compound (b) with N,O-dimethylhydroxylamine or a salt thereof, in the presence of an acid activation agent to produce Compound (c):

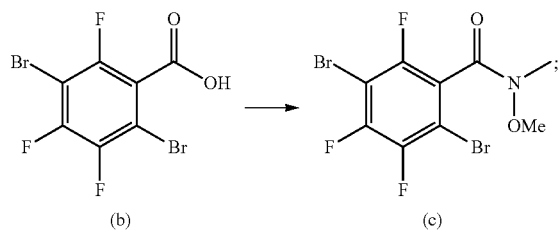 [SMILES: O=C(O)c1c(F)c(Br)c(F)c(F)c1Br ; CON(C)C(=O)c1c(F)c(Br)c(F)c(F)c1Br]

(iii) reacting Compound (c) with a reducing reagent to produce Compound (d):

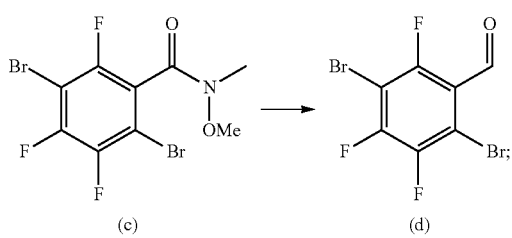 [SMILES: CON(C)C(=O)c1c(F)c(Br)c(F)c(F)c1Br ; O=Cc1c(F)c(Br)c(F)c(F)c1Br]

(iv) reacting Compound (d) with Compound (d-1)

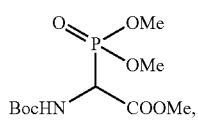

to yield Compound (e):

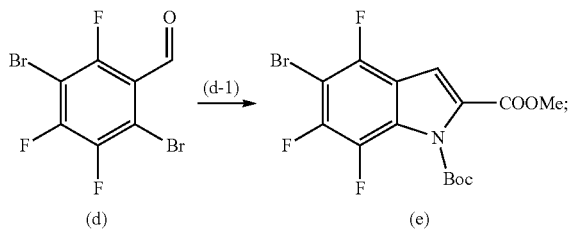 [SMILES: O=Cc1c(F)c(Br)c(F)c(F)c1Br ; COC(=O)c1cc2c(F)c(Br)c(F)c(F)c2n1C(=O)OC(C)(C)C]

(v) reacting Compound (e) with a hydrogen source, such as H₂, ammonium formate, or cyclohexa-1,4-diene, to produce Compound (f):

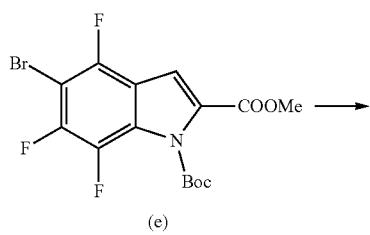

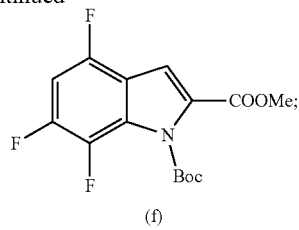

and (vi) Hydrolyzing Compound (f) to produce Compound (1):

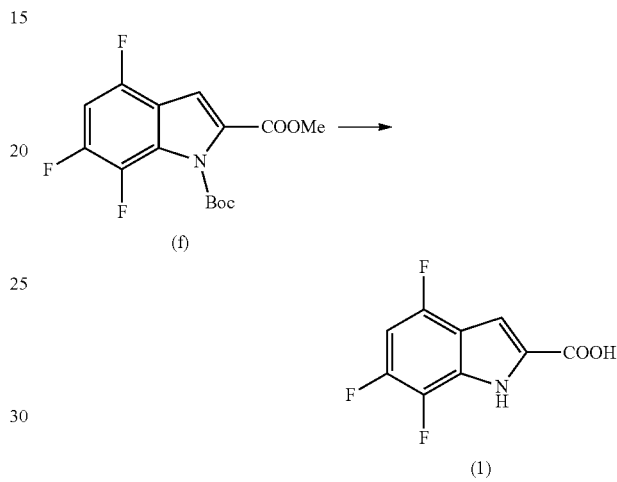

Step (i)

In preferred embodiments, step (i) occurs in a solvent. Suitable solvents include, but are not limited to, sulfuric acid, acetic acid, trifluoromethyl sulfonic acid, acetonitrile, acetone, chloroform, dichloromethane, dimethyl formamide, dimethyl sulfoxide, dioxane, ethyl acetate, heptane, hexane, methanol, methyl t-butyl ether, tetrachloromethane, tetrahydrofuran, and toluene, or a mixture of two or more thereof. Preferably the solvent is sulfuric acid.

In certain embodiments, the bromination agent is bromine, bromine trifluoride, N-bromoacetamide, 1,3-dibromo-5,5-dimethylhydantoin (dibromantin or DBH or DBDMH), 1-bromopyrrolidine-2,5-dione (N-bromosuccinimide; 1-NBS)), N-bromosaccharin (NBSac), 2,2-dibromo-2-cyano-acetamide, 5,5-dibromo-2,2-dimethyl-4,6-dioxo-1,3-dioxane, monopyridin-1-ium tribromide (PyHBr₃), sodium monobromoisocyanurate, tetrabromomethane, tribromoisocyanuric acid, or the like. The bromination agent is preferably 1,3-dibromo-5,5-dimethylhydantoin.

In one embodiment, the reaction is conducted at a temperature from about −20° C. to about 20° C., preferably from about −5° C. to about 5° C. In one embodiment, the reaction takes place over a period from about 15 hours to about 36 hours, preferably about 28 hours.

In a preferred embodiment, the process of the invention further comprises isolating Compound (b), preferably in a substantially pure form.

Step (ii)

In preferred embodiments, step (ii) occurs in an aprotic solvent. Suitable aprotic solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, and toluene, or a mixture of two or more thereof. Preferably the aprotic solvent is dichloromethane.

In certain embodiments, the acid activation agent is acetic anhydride, pivaloyl chloride, ethyl chloroformate (ECF), isobutyl chloroformate (IBCF), Boc anhydride, or di-tert-butyl dicarbonate ($Boc_2O$), 2-ethoxy-1-ethoxycarbonyl-1,2-dihydroquinoline, methanesulfonyl chloride (MsCl), p-toluenesulfonyl chloride (TsCl), n-propanephosphonic acid anhydride (T3P), ethylmethylphosphinic anhydride (EMPA), 1,1'-carbonyldiimidazole (CDI), N,N'-dicyclohexylcarbodiimide (DCC), N,N'-diisopropylcarbodiimide (DIC), (1-ethyl-3-(3'-dimethylaminopropyl)-carbodiimide hydrochloride (EDC), 1-hydroxy-7-azabenzotriazole (HOAt), 1-hydroxybenzotriazole (HOBt), ((benzotriazol-1-yloxy)tris-(dimethylamino)phosphonium hexafluorophosphate (BOP), N-[(dimethylamino)-1H-1,2,3-triazolo[4,5-b]pyridin-1-ylmethylene]-N-methylmethanaminium hexafluorophosphate N-oxide (HATU), N-[(1Hbenzotriazol-1-yl) (dimethylamino)methylene]-N-methylmethanaminiumtetrafluoroborate N-oxide (TBTU), 2-(2-oxo-1(2H)-pyridyl-1,1,3,3-tetramethyluronium tetrafluoroborate (TPTU), 0-[(cyano(ethoxycarbonyl)methyleneamino]-N,N,N',N'-tetramethyluronium tetrafluoroborate (TOTU), N-[(1H-benzotriazol-1-yl) (dimethylamino)-methylene]-N-methylmethanaminium hexafluorophosphate N-oxide (HBTU), cyanuric chloride, 2-chloro-4,6-dimethoxy-1,3,5-triazine (CDMT), 4-(4,6-dimethoxy-1,3,5-triazin-2-yl)-4-methylmorpholinium chloride (DMTMM), or boric acid.

In certain embodiments, the acid activation agent is a chlorination agent, such as sulfonic chloride, thionyl chloride ($SOCl_2$), oxalyl chloride, ($(COCl)_2$), phosphorus oxychloride ($POCl_3$), and Vilsmeier reagent or the like. A preferred chlorination agent is oxalyl chloride.

Preferably, N,O-dimethylhydroxylamine is used in step (ii) in the form of the hydrochloride salt.

In certain embodiments, step (ii) occurs in the presence of a catalyst, such as, but not limited to, N,N-dimethylformamide, optionally in the presence of a suitable base, such as, but not limited to, triethylamine, diisopropylethylamine, or N-methylmorpholine. A preferred base is triethylamine.

Step (ii) is conducted at a suitable temperature, such as, for example, from about 0° C. to about 40° C., preferably about 25° C. In certain embodiments, step (ii) takes place over a period from about 1 hour to about 5 hours, preferably about 1 hour.

In preferred embodiments, the process of the invention further comprises isolating Compound (c), preferably in a substantially pure form.

Step (iii)

In preferred embodiments, step (iii) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and a mixture of two or more thereof. A preferred solvent is dichloromethane.

The reducing agent can be any suitable reducing agent, such as lithium aluminum hydride or diisobutylaluminum hydride.

Step (iii) is carried out at a suitable temperature, such as, for example, from about −80° C. to about −40° C., preferably from about −70° C. to about −60° C. In certain embodiments, step (iii) takes place for a period from about 0.5 hour to about 5 hours, preferably about 1.5 hours.

In preferred embodiments, the process of the invention further comprises isolating Compound (d), preferably in a substantially pure form.

Step (iv)

In preferred embodiments, step (iv) occurs in a solvent. Suitable solvents include, but are not limited to, acetonitrile, acetone, dichloromethane, dichloroethane, dimethyl formamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. A preferred solvent is dichloromethane.

In certain embodiments, step (iv) occurs in the presence of a catalyst. Suitable catalysts include, but are not limited to, cuprous iodide, copper (I) oxide, and [1,1'-bis(diphenylphosphino)ferrocene] palladium (II) dichloride, optionally in the presence of a ligand, such as, but not limited to, 2,2'-bipyridine or (S)-proline.

In certain embodiments, step (iv) occurs in the presence of a suitable base, such as, but not limited to, potassium phosphate tribasic, sodium phosphate tribasic, potassium carbonate, sodium carbonate, cesium carbonate, triethylamine, di-isopropylethylamine, N-methylmorpholine, potassium acetate or a combination of two or more thereof. Preferably the base is potassium phosphate tribasic.

In certain embodiments, step (iv) occurs in the presence of a catalyst, a ligand, and a base. Preferably the catalyst is cuprous iodide, the ligand is 2,2'-bipyridine and the base is potassium phosphate tribasic. Preferably the molar ratio of cuprous iodide and 2,2'-bipyridine is about 1:1.

Step (iv) is carried out at a suitable temperature, such as for example from about 0° C. to about 100° C., preferably from about 0° C. to about 40° C., and more preferably about 25° C. In one embodiment, step (iv) takes place for a period from about 10 hours to about 20 hours, preferably about 15 hours.

In preferred embodiments, the process of the invention further includes isolating Compound (e), preferably in a substantially pure form.

Step (v)

In preferred embodiments, step (v) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, and toluene, and mixtures of two or more thereof. A preferred solvent is methanol.

In certain embodiments, step (v) occurs in the presence of a catalyst. Suitable catalysts include, but are not limited to, palladium on carbon, palladium hydroxide on carbon, or Raney nickel. Preferably the catalyst is palladium on carbon (5-10 mol %).

In certain embodiments, step (v) is carried out at a suitable hydrogen pressure, such as, but not limited to, from about 0.5 atm to about 3 atm, preferably about 1 atm.

Step (v) is carried out at a suitable temperature, such as, for example, from about 0° C. to about 40° C., preferably about 25° C. In one embodiment, step (v), the reaction takes place over a period from about 8 hours to about 20 hours, preferably about 14 hours.

In preferred embodiments, the process of the invention further comprises isolating Compound (f), preferably in a substantially pure form.

Step (vi)

Step (vi) preferably occurs in the presence of a solvent. Suitable solvents include acetonitrile, acetone, dichloromethane, dimethyl formamide, dimethyl sulfoxide, dioxane, heptane, hexane, methanol, methyl t-butyl ether, tetrahydrofuran, and toluene, or a mixture of two or more thereof, optionally in the present of a co-solvent. Preferably the solvent is methyl t-butyl ether. More preferably the solvent is methyl t-butyl ether and the co-solvent is $H_2O$.

In certain embodiments, step (vi) occurs in the presence of a base to remove the Boc group and methyl ester. Suitable bases include, but are not limited to, sodium hydroxide, potassium hydroxide, lithium hydroxide, and combinations of two or more thereof. A preferred base is sodium hydroxide. After the saponification reaction, Compound (1) is formed by treatment with an acid, such as, but not limited to, hydrogen chloride, hydrogen bromide, sulfuric acid or a combination of two or more thereof. A preferred acid is hydrogen chloride.

Step (vi) is carried out at a suitable temperature, such as, for example, from about 30° C. to about 100° C., preferably from about 55° C. to about 65° C. In one embodiment, the invention relates to step (vi), the reaction takes place over a period from about 1 hours to about 20 hours, preferably from about 3 hours to about 6 hours.

In preferred embodiments, the process of the invention further comprises isolating Compound (1), preferably in a substantially pure form.

In certain embodiments, the invention provides a method of producing the Compound (d) comprising steps (i), (ii), and (iii) described above.

In certain embodiments, the invention provides a method of producing Compound (d) comprising steps of:

(i') reacting Compound (a), 2,4,5-trifluorobenzoic acid, with a bromination agent, to produce Compound (b):

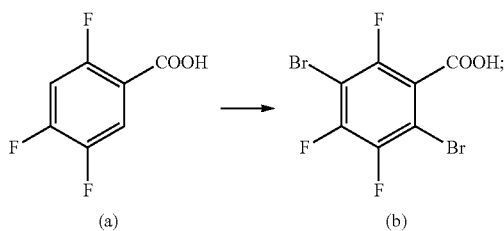 [SMILES: O=C(O)c1cc(F)c(F)cc1F ; O=C(O)c1c(F)c(Br)c(F)c(F)c1Br]

(ii') reacting Compound (b) with an acid activation reagent and a reducing agent to produce Compound (c-1), (2,5-dibromo-3,4,6-trifluorophenyl) methanol:

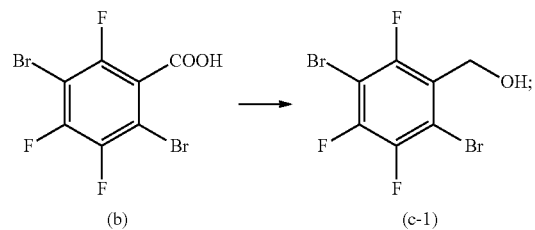 [SMILES: O=C(O)c1c(F)c(Br)c(F)c(F)c1Br ; OCc1c(F)c(Br)c(F)c(F)c1Br]

and (iii') reacting Compound (c-1) with an oxidizing agent to produce Compound (d), 2,5-dibromo-3,4,6-trifluorobenzaldehyde:

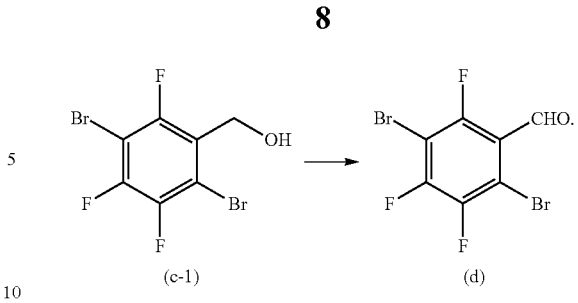

Step (i')

In preferred embodiments, step (i') occurs in a solvent. Suitable solvents include, but are not limited to, sulfuric acid, acetic acid, trifluoromethyl sulfonic acid, acetonitrile, acetone, chloroform, dichloromethane, dimethyl formamide, dimethyl sulfoxide, dioxane, ethyl acetate, heptane, hexane, methanol, methyl t-butyl ether, tetrachloromethane, tetrahydrofuran, and toluene, or a mixture of two or more thereof. Preferably the solvent is sulfuric acid.

In certain embodiments, the bromination agent is bromine, bromine trifluoride, N-bromoacetamide, 1,3-dibromo-5,5-dimethylhydantoin (dibromantin or DBH or DBDMH), 1-bromopyrrolidine-2,5-dione (N-bromosuccinimide; 1-NBS)), N-bromosaccharin (NBSac), 2,2-dibromo-2-cyano-acetamide, 5,5-dibromo-2,2-dimethyl-4,6-dioxo-1,3-dioxane, monopyridin-1-ium tribromide ($PyHBr_3$), sodium monobromoisocyanurate, tetrabromomethane, tribromoisocyanuric acid, or the like. The bromination agent is preferably 1,3-dibromo-5,5-dimethylhydantoin.

In one embodiment, the reaction is conducted at a temperature from about −20° C. to about 20° C., preferably from about −5° C. to about 5° C. In one embodiment, the reaction takes place over a period from about 15 hours to about 36 hours, preferably about 28 hours.

In a preferred embodiment, the process of the invention further comprises isolating Compound (b), preferably in a substantially pure form.

Step (ii')

In preferred embodiments, the acid activation in step (ii') occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and a mixture of two or more thereof. A preferred solvent in acid activation is dichloromethane.

The acid activation reagent can be any suitable agent, such as but not limited to, oxalyl chloride, sulfonyl chloride, 1-chloro-N,N,2-trimethyl-1-propenylamine, isobutyl chloroformate, isopropyl chloroformate, hydroxybenzotriazole (HOBt), or the like. Preferred acid activation reagents include suitable acid chloride formation reagents, such as oxalyl chloride, sulfonyl chloride, 1-chloro-N,N,2-trimethyl-1-propenylamine, or the like. A preferred acid activation reagent is oxalyl chloride.

Acid activation in step (ii') is carried out at a suitable temperature, such as, for example, from about 0° C. to about 100° C., preferably from about 0° C. to about 50° C., more preferably about 25° C. In certain embodiments, the acid activation in step (ii') takes place for a period from about 1 hour to about 24 hours, preferably about 2 hours.

In preferred embodiments, the reduction in step (ii') occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and a mixture of two or more thereof. A preferred solvent is tetrahydrofuran.

The reducing agent can be any suitable reducing agent, such as but not limited to, lithium aluminum hydride, lithium borohydride, sodium borohydride, diisobutylaluminum hydride, borane-tetrahydrofuran complex, borane-dimethyl sulfide complex, or the like. Preferably the reducing agent is lithium borohydride.

The reduction in step (ii') is carried out at a suitable temperature, such as, for example, from about −20° C. to about 30° C., preferably from about −10° C. to about 10° C., more preferably about 0° C. In certain embodiments, the reduction in step (ii') takes place for a period from about 30 minutes to about 5 hours, preferably about 1 hours.

In preferred embodiments, the process of the invention further comprises isolating Compound (c-1), preferably in a substantially pure form.

Step (iii')

In preferred embodiments, step (iii') occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and a mixture of two or more thereof. A preferred solvent is dichloromethane.

In one embodiment, suitable oxidizing agents include, but are not limited to, trichloroisocyanuric acid with TEMPO, sodium hypochlorite with TEMPO, oxalyl chloride with dimethyl sulfoxide, manganese oxide, chromiumtrioxide, pyridinium chlorochromate, sodium perchloride, Dess-Martin periodinane, or the like. A preferred oxidizing agent is trichloroisocyanuric acid with TEMPO.

In one embodiment, step (iii') is conducted at a temperature from about −20° C. to about 50° C., preferably from about −10° C. to about 10° C., and more preferably about 0° C. In certain embodiments, step (iii') takes place for a period from about 10 minutes to about 10 hours, preferably about 30 minutes.

In preferred embodiments, the process of the invention further comprises isolating Compound (d), preferably in a substantially pure form.

In certain embodiments, the invention provides a method of producing Compound (d) comprising steps (ii) and (iii) described above.

In certain embodiments, the invention provides a method of producing Compound (d) comprising steps (ii') and (iii') described above.

In a principal embodiment, the present invention provides a process for the preparation of Compound (1),

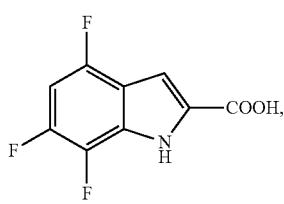

the process comprising the steps of:
(a-1) reacting Compound (d) with a compound of Formula (D-1)

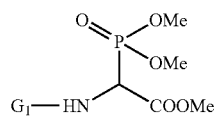

to yield a compound of Formula (E):

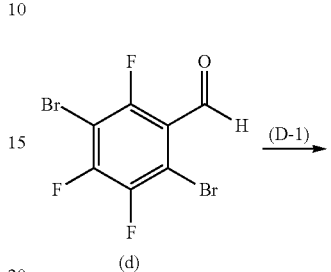

wherein $G_1$ is -Boc, -Cbz, —C(O)OMe, —C(O)OEt, -Fmoc, -Troc, -Moz, -Pnz, -Teoc, -Ac, or -Bz;

(a-2a) hydrolyzing Compound (E) to produce Compound (g):

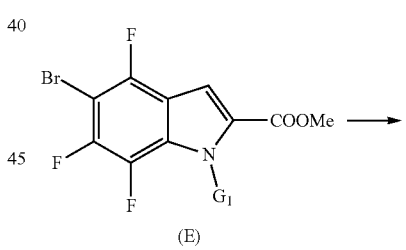

and (a-3a) reacting Compound (g) with a hydrogen source, such as $H_2$, ammonium formate, or cyclohexa-1,4-diene, in the presence of a hydrogenation catalyst, to produce Compound (1):

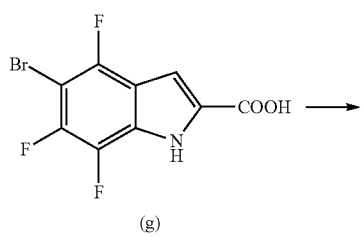

(g)

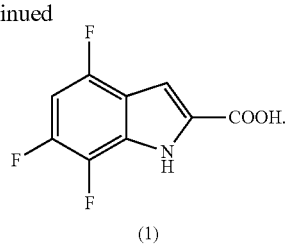

(1)

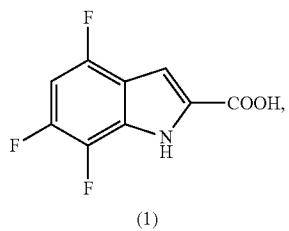

(1)

alternatively, steps (a-2a) and (a-3a) are replaced by steps (a-2b) and (a-3b): (a-2b) reacting the compound of Formula (E) with a hydrogen source, such as $H_2$, ammonium formate, or cyclohexa-1,4-diene, in the presence of a hydrogenation catalyst, to produce a compound of Formula (F):

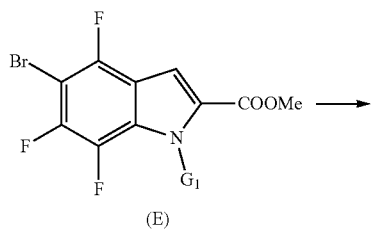

(E)

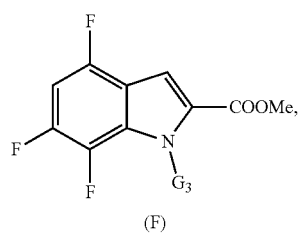

(F)

wherein $G_3$ is -Boc, —C(O)OMe, —C(O)OEt, -Troc, -Teoc, —Ac, -Bz or hydrogen; and (a-3b) hydrolyzing the compound of Formula (F) to produce Compound (1)

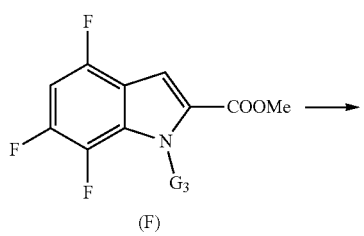

(F)

Step (a-1)

In preferred embodiments, step (a-1) occurs in a solvent. Suitable solvents include, but are not limited to, acetonitrile, acetone, dichloromethane, dichloroethane, dimethyl formamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. A preferred solvent is dichloromethane.

In certain embodiments, step (a-1) occurs in the presence of a catalyst. Suitable catalysts include, but are not limited to, cuprous iodide, copper (I) oxide, copper(I) thiophene-2-carboxylate, and [1,1'-bis(diphenylphosphino)ferrocene] palladium (II) dichloride, optionally in the presence of a ligand, such as, but not limited to, 2,2'-bipyridine, 1,10-phenanthroline, or (S)-proline.

In certain embodiments, step (a-1) occurs in the presence of a suitable base. Suitable bases include, but are not limited to, sodium carbonate, sodium bicarbonate, sodium hydroxide, sodium phosphonate dibasic, sodium phosphate tribasic, sodium phosphate dibasic, sodium acetate, sodium citrate, potassium carbonate, potassium bicarbonate, potassium hydroxide, potassium phosphonate dibasic, potassium phosphate tribasic, potassium phosphate dibasic, potassium acetate, potassium citrate, lithium carbonate, lithium bicarbonate, lithium hydroxide, lithium phosphonate dibasic, lithium phosphate tribasic, lithium phosphate dibasic, lithium acetate, lithium citrate, cesium sodium carbonate, cesium bicarbonate, cesium hydroxide, cesium phosphonate dibasic, cesium phosphate tribasic, cesium phosphate dibasic, cesium acetate, cesium citrate, triethylamine, di-isopropylethylamine, N-methylmorpholine, or a combination of two or more thereof. Preferably the base is potassium phosphate tribasic, sodium phosphate tribasic, potassium carbonate, sodium carbonate, cesium carbonate, triethylamine, di-isopropylethylamine, N-methylmorpholine, potassium acetate or a combination of two or more thereof. More preferably the base is potassium phosphate tribasic.

In certain embodiments, step (a-1) occurs in the presence of a catalyst, a ligand, and a base. Preferably the catalyst is cuprous iodide, the ligand is 2,2'-bipyridine or 1,10-phenanthroline, and the base is potassium phosphate tribasic. Preferably the molar ratio of cuprous iodide and 2,2'-bipyridine or 1,10-phenanthroline is about 1:1.

Step (a-1) is carried out at a suitable temperature, such as from about 0° C. to about 100° C., preferably from about 0° C. to about 40° C., and more preferably about 25° C. In one embodiment, step (a-1) takes place for a period from about 10 hours to about 20 hours, preferably about 15 to 18 hours.

In preferred embodiments, the process of the invention further includes isolating the compound of Formula (E), preferably in a substantially pure form.

Step (a-2a)

Step (a-2a) preferably occurs in the presence of a solvent. Suitable solvents include acetonitrile, acetone, dichloromethane, dimethyl formamide, dimethyl sulfoxide, dioxane, heptane, hexane, methanol, methyl t-butyl ether, tetrahydrofuran, water, and toluene, or a mixture of two or more thereof, optionally in the present of a co-solvent. Preferably the solvent is tetrahydrofuran, and the co-solvent is water. Preferably the volume ratio of tetrahydrofuran to water is about 2:5.

In certain embodiments, step (a-2a) occurs in the presence of a base to remove the -$G_1$ group and to hydrolyze the methyl ester. Suitable bases include, but are not limited to, sodium hydroxide, potassium hydroxide, lithium hydroxide, and combinations of two or more thereof. A preferred base is sodium hydroxide. After the saponification reaction, Compound (g) is formed by treatment with an acid, such as, but not limited to, hydrogen chloride, hydrogen bromide, sulfuric acid or a combination of two or more thereof. A preferred acid is hydrogen chloride.

Step (a-2a) is carried out at a suitable temperature, such as, for example, from about 30° C. to about 100° C., preferably from about 60° C. to about 70° C. In one embodiment, the invention relates to step (a-2a), the reaction takes place over a period from about 1 hours to about 3 days, preferably about 16 hours.

Preferably, the process of the invention further comprises isolating Compound (g), preferably in substantially pure form.

Step (a-3a)

In preferred embodiments, step (a-3a) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, and toluene, and mixtures of two or more thereof. A preferred solvent is ethanol.

In certain embodiments, step (a-3a) occurs in the presence of a catalyst. Suitable catalysts include, but are not limited to, palladium on carbon, palladium hydroxide on carbon, or Raney nickel. Preferably the catalyst is palladium on carbon.

In certain embodiments, step (a-3a) occurs in the presence of a suitable base. Suitable bases include, but are not limited to, sodium carbonate, sodium bicarbonate, sodium hydroxide, sodium phosphonate dibasic, sodium phosphate tribasic, sodium phosphate dibasic, sodium acetate, sodium citrate, potassium carbonate, potassium bicarbonate, potassium hydroxide, potassium phosphonate dibasic, potassium phosphate tribasic, potassium phosphate dibasic, potassium acetate, potassium citrate, lithium carbonate, lithium bicarbonate, lithium hydroxide, lithium phosphonate dibasic, lithium phosphate tribasic, lithium phosphate dibasic, lithium acetate, lithium citrate, cesium sodium carbonate, cesium bicarbonate, cesium hydroxide, cesium phosphonate dibasic, cesium phosphate tribasic, cesium phosphate dibasic, cesium acetate, cesium citrate, triethylamine, di-isopropylethylamine, N-methylmorpholine, or a combination of two or more thereof. Preferably the base is sodium carbonate.

In certain embodiments, step (a-3a) is carried out at a suitable hydrogen pressure, such as, but not limited to, from about 0.5 atm to about 3 atm, preferably about 1 atm.

Step (a-3a) is carried out at a suitable temperature, such as, for example, from about 0° C. to about 100° C., preferably about 20° C. to about 30° C. In one embodiment, step (a-3a), the reaction takes place over a period from about 1 day to about 10 days, preferably about 42 hours.

In preferred embodiments, the process of the invention further comprises isolating Compound (1), preferably in substantially pure form.

Step (a-2b)

In preferred embodiments, step (a-2b) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, and toluene, and mixtures of two or more thereof. A preferred solvent is ethanol.

In certain embodiments, step (a-2b) occurs in the presence of a catalyst. Suitable catalysts include, but are not limited to, palladium on carbon, palladium hydroxide on carbon, or Raney nickel. Preferably the catalyst is palladium on carbon.

In certain embodiments, step (a-2b) occurs in the presence of a suitable base. Suitable bases include, but are not limited to, sodium carbonate, sodium bicarbonate, sodium hydroxide, sodium phosphonate dibasic, sodium phosphate tribasic, sodium phosphate dibasic, sodium acetate, sodium citrate, potassium carbonate, potassium bicarbonate, potassium hydroxide, potassium phosphonate dibasic, potassium phosphate tribasic, potassium phosphate dibasic, potassium acetate, potassium citrate, lithium carbonate, lithium bicarbonate, lithium hydroxide, lithium phosphonate dibasic, lithium phosphate tribasic, lithium phosphate dibasic, lithium acetate, lithium citrate, cesium sodium carbonate, cesium bicarbonate, cesium hydroxide, cesium phosphonate dibasic, cesium phosphate tribasic, cesium phosphate dibasic, cesium acetate, cesium citrate, triethylamine, di-isopropylethylamine, N-methylmorpholine, or a combination of two or more thereof. Preferably the base is sodium carbonate.

In certain embodiments, step (a-2b) is carried out at a suitable hydrogen pressure, such as, but not limited to, from about 0.5 atm to about 3 atm, preferably about 1 atm.

Step (a-2b) is carried out at a suitable temperature, such as, for example, from about 0° C. to about 40° C., preferably about 25° C. In one embodiment, step (a-2b), the reaction takes place over a period from about 8 hours to about 20 hours, preferably about 14 hours.

Preferably, the process of the invention further comprises isolating the compound of Formula (f), preferably in substantially pure form.

Step (a-3b)

Step (a-3b) preferably occurs in the presence of a solvent. Suitable solvents include acetonitrile, acetone, dichloromethane, dimethyl formamide, dimethyl sulfoxide, dioxane, heptane, hexane, methanol, methyl t-butyl ether, tetrahydrofuran, water, and toluene, or a mixture of two or more thereof, optionally in the present of a co-solvent. Preferably the solvent is methyl t-butyl ether. More preferably the solvent is methyl t-butyl ether and the co-solvent is water. Preferably the volume ratio of methyl t-butyl ether to water is about 2:5.

In certain embodiments, step (a-3b) occurs in the presence of a base to remove the Boc group and methyl ester. Suitable bases include, but are not limited to, sodium hydroxide, potassium hydroxide, lithium hydroxide, and combinations of two or more thereof. A preferred base is sodium hydroxide. After the saponification reaction, products are formed by treatment with an acid, such as, but not limited to, hydrogen chloride, hydrogen bromide, sulfuric acid or a combination of two or more thereof. A preferred acid is hydrogen chloride.

Step (a-3b) is carried out at a suitable temperature, such as, for example, from about 30° C. to about 100° C., preferably from about 55° C. to about 65° C. In one embodiment, the invention relates to step (a-3b), the reaction takes place over a period from about 1 hours to about 20 hours, preferably from about 3 hours to about 6 hours.

Preferably, the process of the invention further comprises isolating Compound (1), preferably in substantially pure form.

In another embodiment, the present invention provides a process for the preparation of Compound (1)

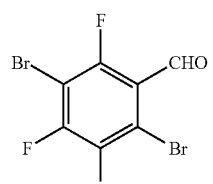

(1)

the process comprising the steps of:

(a-i) reacting Compound (d) with 2-benzamidoacetic acid (also named hippuric acid) to produce Compound (h-Int):

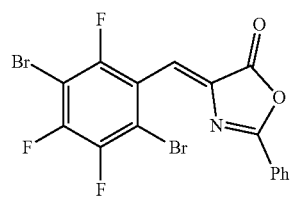

(d)

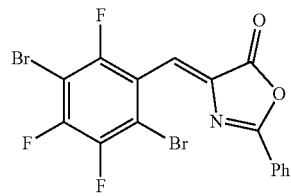

(h-Int)

(a-ii) converting Compound (h-Int) to Compound (h), methyl 2-benzamido-3-(2,5-dibromo-3,4,6-trifluorophenyl)acrylate:

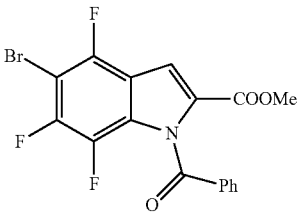

(h-Int)

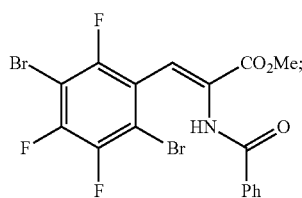

(h)

(a-iii) converting Compound (h) to Compound (i), methyl 1-benzoyl-5-bromo-4,6,7-trifluoro-1H-indole-2-carboxylate:

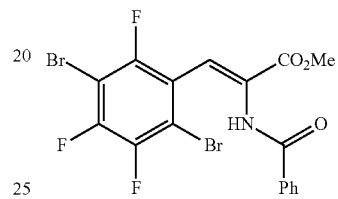

(h)

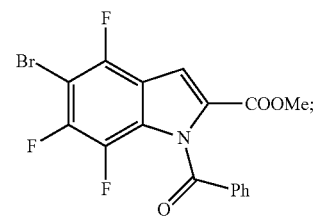

(i)

(a-iv) converting Compound (i) to Compound (j-Int):

(i)

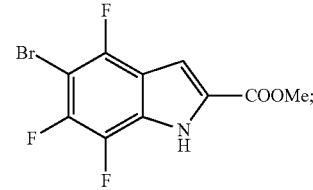

(j-Int)

(a-v) converting Compound (j-Int) to Compound (j):

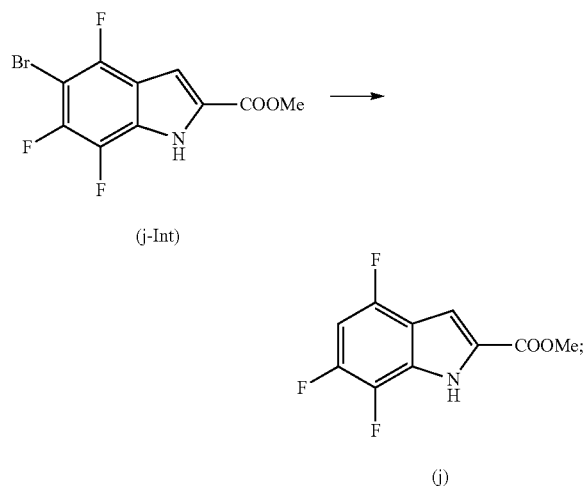

(j-Int)

(j)

and
(a-vi) hydrolyzing Compound (j) to produce Compound (1):

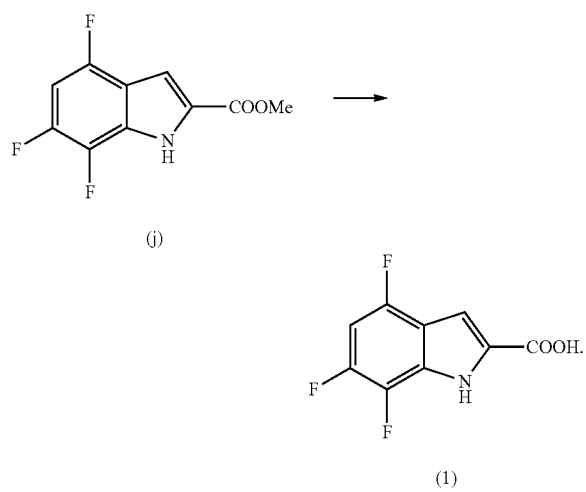

(j)

(1)

Step (a-i)

In preferred embodiments, step (a-i) occurs in a solvent. Suitable solvents include, but are not limited to, acetonitrile, acetone, dichloromethane, dichloroethane, dimethyl formamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. Preferably the solvent is toluene.

In certain embodiments, step (a-i) occurs in the presence of an acid activation agent, such as, but not limited to, acetic anhydride, pivaloyl chloride, ethyl chloroformate (ECF), isobutyl chloroformate (IBCF), Boc anhydride, or di-tert-butyl dicarbonate ($Boc_2$), 2-ethoxy-1-ethoxycarbonyl-1,2-dihydroquinoline, methanesulfonyl chloride (MsCl), p-toluenesulfonyl chloride (TsCl), n-propanephosphonic acid anhydride (T3P), ethylmethylphosphinic anhydride (EMPA), 1,1'-carbonyldiimidazole (CDI), N,N'-dicyclohexylcarbodiimide (DCC), N,N'-diisopropylcarbodiimide (DIC), (1-ethyl-3-(3'-dimethylaminopropyl)-carbodiimide hydrochloride (EDC), 1-hydroxy-7-azabenzotriazole (HOAt), 1-hydroxybenzotriazole (HOBt), ((benzotriazol-1-yloxy)tris-(dimethylamino)phosphonium hexafluorophosphate (BOP), N-[(dimethylamino)-1H-1,2,3-triazolo[4,5-b]pyridin-1-ylmethylene]-N-methylmethanaminium hexafluorophosphate N-oxide (HATU), N-[(1Hbenzotriazol-1-yl)-(dimethylamino)methylene]-N-methylmethanaminiumtetrafluoroborate N-oxide (TBTU), 2-(2-oxo-1 (2H)-pyridyl-1,1,3,3-tetramethyluronium tetrafluoroborate (TPTU), O -[(cyano(ethoxycarbonyl)methyleneamino]-N, N,N,N'-tetramethyluronium tetrafluoroborate (TOTU), N-[(1H-benzotriazol-1-yl) (dimethylamino)-methylene]-N-methylmethanaminium hexafluorophosphate N-oxide (HBTU), cyanuric chloride, 2-chloro-4,6-dimethoxy-1,3,5-triazine (CDMT), 4-(4,6-dimethoxy-1,3,5-triazin-2-yl)-4-methylmorpholinium chloride (DMTMM), or boric acid. Preferably the acid activation agent is acetic anhydride.

In preferred embodiments, step (a-i) is carried out at a suitable temperature, such as for example from about 80° C. to about 120° C., preferably from about 100° C. to about 105° C., and more preferably about 105° C. In one embodiment, step (a-i) takes place for a period from about 1 hour to about 24 hours, preferably about 4 hours.

In a preferred embodiment of step (a-i), Compound (h-Int) is not isolated and is used directly in the next step.

Step (a-ii)

In certain embodiments, the methyl ester formation in step (a-ii) occurs in a solvent. Suitable solvents include, but are not limited to, acetonitrile, acetone, dichloromethane, dichloroethane, dimethyl formamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. Preferably the solvent is dichloromethane.

In certain embodiments, the methyl ester formation in step (a-ii) is carried out at a suitable temperature, such as for example from about 0° C. to about 100° C., preferably from about 0° C. to about 40° C., and more preferably about 20° C. In one embodiment, the methyl ester formation in step (a-ii) takes place for a period from about 1 hour to about 24 hours, preferably about 2 hours.

In preferred embodiments, the process of the invention further includes isolating Compound (h), preferably in substantially pure form.

Step (a-iii)

In preferred embodiments, step (a-iii) occurs in a solvent. Suitable solvents include, but are not limited to, acetonitrile, acetone, dichloromethane, dichloroethane, dimethyl formamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. A preferred solvent is toluene.

In certain embodiments, step (a-iii) occurs in the presence of a catalyst. Suitable catalysts include, but are not limited to, cuprous iodide, copper (I) oxide, copper(I) thiophene-2-carboxylate, and [1,1'-bis(diphenylphosphino)ferrocene] palladium (II) dichloride, optionally in the presence of a ligand, such as, but not limited to, 2,2'-bipyridine, 1,10-phenanthroline, or (S)-proline.

In certain embodiments, step (a-iii) occurs in the presence of a suitable base. Suitable bases include, but are not limited to, sodium carbonate, sodium bicarbonate, sodium hydroxide, sodium phosphonate dibasic, sodium phosphate tribasic, sodium phosphate dibasic, sodium acetate, sodium citrate, potassium carbonate, potassium bicarbonate, potassium hydroxide, potassium phosphonate dibasic, potassium phosphate tribasic, potassium phosphate dibasic, potassium acetate, potassium citrate, lithium carbonate, lithium bicarbonate, lithium hydroxide, lithium phosphonate dibasic, lithium phosphate tribasic, lithium phosphate dibasic, lithium acetate, lithium citrate, cesium sodium carbonate, cesium bicarbonate, cesium hydroxide, cesium phosphonate dibasic, cesium phosphate tribasic, cesium phosphate dibasic, cesium acetate, cesium citrate, triethylamine, di-isopropylethylamine, N-methylmorpholine, or a combination of two or more thereof. Preferably the base is potassium phosphate tribasic.

In certain embodiments, step (a-iii) occurs in the presence of a catalyst, a ligand, and a base. Preferably the catalyst is cuprous iodide, the ligand is 2,2'-bipyridine and the base is potassium phosphate tribasic. Preferably the molar ratio of cuprous iodide and 2,2'-bipyridine is about 1:1.

In certain embodiments, step (a-iii) is carried out at a suitable temperature, such as, for example, from about 80° C. to about 120° C., preferably from about 100° C. to about 105° C., and more preferably about 105° C. In one embodiment, step (a-iii) takes place for a period from about 1 hour to about 3 days, preferably about 16 hours.

In preferred embodiments, the process of the invention further includes isolating Compound (1), preferably in substantially pure form.

Step (a-iv)

In preferred embodiments, step (a-iv) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, and toluene, and mixtures of two or more thereof. A preferred solvent is dichloromethane.

In certain embodiments, step (a-iv) occurs in the presence of an amine. Suitable amines include, but are not limited to, ethylenediamine, ammonia, ethylamine, propylamine, isopropylamine, butylamine, or the like. Preferably the amine is ethylenediamine.

In certain embodiments, step (a-iv) is carried out at a suitable temperature, such as, for example, from about 0° C. to about 40° C., preferably about 20° C. In one embodiment, step (a-iv), the reaction takes place over a period from about 1 day to about 24 hours, preferably about 8 hours.

In a preferred embodiment of step (a-iv), Compound (j-Int) is not isolated and is taken directly to the next step.

Step (a-v)

In preferred embodiments, reduction in step (a-v) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, and toluene, and mixtures of two or more thereof. A preferred solvent is tetrahydrofuran.

In certain embodiments, reduction in step (a-v) occurs in the presence of a catalyst. Suitable catalysts include, but are not limited to, palladium on carbon, palladium hydroxide on carbon, or Raney nickel. Preferably the catalyst is palladium on carbon.

In certain embodiments, reduction in step (a-v) is carried out at a suitable hydrogen pressure, such as, but not limited to, from about 0.5 atm to about 3 atm, preferably about 1 atm.

Reduction in Step (a-v) is carried out at a suitable temperature, such as, for example, from about 0° C. to about 40° C., preferably about 20° C. In one embodiment, step (a-v), the reaction takes place over a period from about 1 day to about 30 days, preferably about 30 hours.

In preferred embodiments, the process of the invention further comprises isolating Compound (j), preferably in substantially pure form.

Step (a-vi)

In certain embodiments, step (a-vi) preferably occurs in the presence of a solvent. Suitable solvents include acetonitrile, acetone, dichloromethane, dimethyl formamide, dimethyl sulfoxide, dioxane, heptane, hexane, methanol, methyl t-butyl ether, tetrahydrofuran, and toluene, water, or a mixture of two or more thereof, optionally in the present of a co-solvent. Preferably the solvent is methyl t-butyl ether. More preferably the solvent is tetrahydrofuran, and the co-solvent is water. Preferably the volume ratio of tetrahydrofuran to water is about 1:1.

In certain embodiments, step (a-vi) occurs in the presence of a base. Suitable bases include, but are not limited to, sodium hydroxide, potassium hydroxide, lithium hydroxide, and combinations of two or more thereof. A preferred base is sodium hydroxide.

In certain embodiments, step (a-vi) is carried out at a suitable temperature, such as, for example, from about 30° C. to about 100° C., preferably from about 60° C. to about 70° C. In one embodiment, the reaction of step (a-vi) takes place over a period from about 1 hour to about 3 days, preferably about 24 hours.

In certain embodiments of step (a-vi), after hydrolyzing, Compound (1) is formed by treatment with an acid, such as, but not limited to, hydrogen chloride, hydrogen bromide, sulfuric acid or a combination of two or more thereof. A preferred acid is hydrogen chloride.

Preferably, the process of the invention further comprises isolating Compound (1), preferably in substantially pure form.

In another embodiment, the present invention provides a process for the preparation of Compound (1)

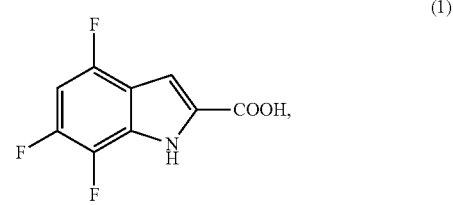 [SMILES: O=C(O)c1cc2c(F)cc(F)c(F)c2[nH]1]

(1)

the process comprising the steps of:
(b-1) reacting Compound (k), 2,3,4,5-tetrafluorobenzoic acid, with a defluorination agent, to produce Compound (1), 2,3,5-trifluorobenzoic acid:

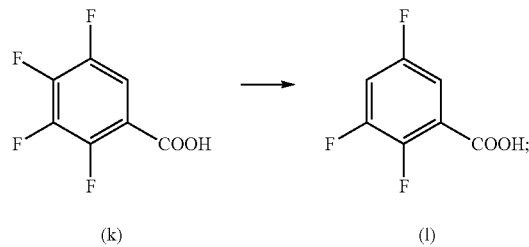 [SMILES: O=C(O)c1cc(F)c(F)c(F)c1F ; O=C(O)c1cc(F)cc(F)c1F]

(b-2) reacting Compound (1) under Curtius Rearrangement conditions, to produce Compound (m), tert-butyl (2,3,5-trifluorophenyl)carbamate:

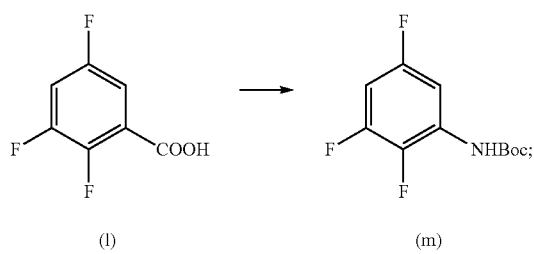 [SMILES: O=C(O)c1cc(F)cc(F)c1F ; CC(C)(C)OC(=O)Nc1cc(F)cc(F)c1F]

(l)　　　　　(m)

(b-3) reacting Compound (m) with a protecting agent to produce the compound of Formula (N):

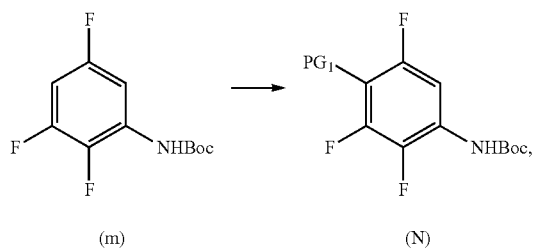

(m)　　　　　(N)

wherein $PG_1$ is selected from -TMS, —Cl, and —Br;

(b-4) reacting the compound of Formula (N) with a formylation agent to produce a compound of Formula (P):

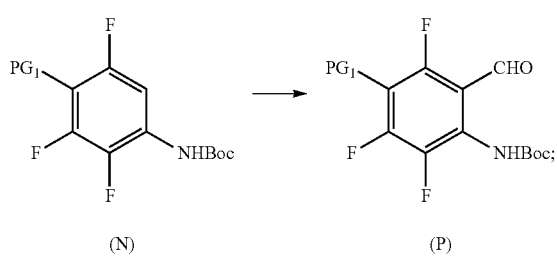

(N)　　　　　(P)

(b-5) reacting the compound of Formula (P) with a compound of Formula (D-2):

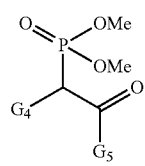

(D-2)

to yield a compound of Formula (Q):

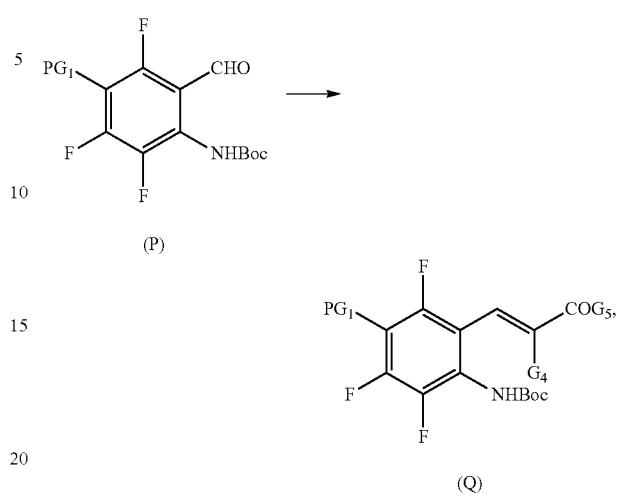

(P)

(Q)

wherein $G_4$ and $G_5$ are both independently —$C_1$-$C_4$ alkoxyl; (b-6) reacting the compound of Formula (Q) with an acid to produce a compound of Formula (R):

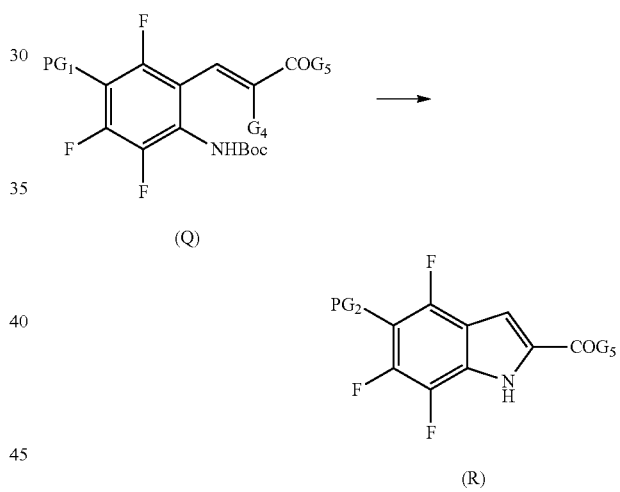

(Q)

(R)

wherein $PG_2$ is —Cl, —Br or hydrogen;

(b-7a) if $PG_2$ is —Cl or —Br, reacting the compound of Formula (R) with a reducing agent to produce a compound of Formula (R-1):

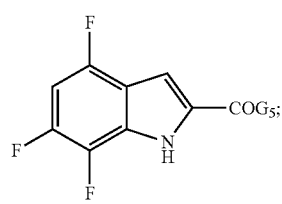

and (b-7) reacting the compound of Formula (R-1) with a base to produce Compound (1):

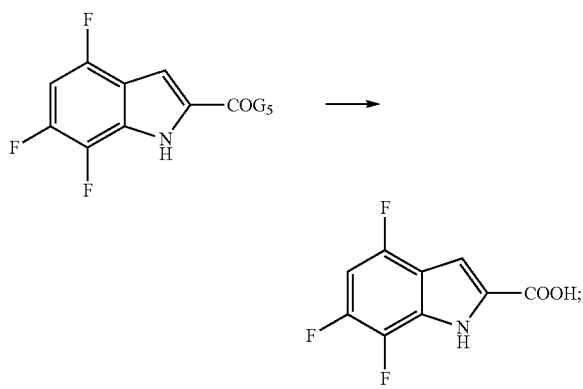

Step (b-1)

In preferred embodiments, step (b-1) occurs in the presence of ammonia.

In certain embodiments, the defluorination agent is a metal, a metal oxide, or a metal complex, such as zinc, magnesium, alumina, or the like. Preferably, the defluorination agent is zinc.

In one embodiment, the reaction is conducted at a temperature from about 0° C. to about 100° C., preferably from about 0° C. to about 40° C., and more preferably about 25° C. In one embodiment, step (b-1) takes place for a period from about 1 hour to about 10 days, preferably about 1 day to about 5 days, and more preferably about 3 days. In a preferred embodiment, the process of the invention further comprises isolating Compound (b), preferably in a substantially pure form.

Step (b-2)

In certain embodiments, step (b-2) occurs in a solvent. Suitable solvents include, but are not limited to, t-butyl alcohol, acetonitrile, acetone, dichloromethane, chloroform, dimethyl formamide, dimethyl sulfoxide, dioxane, ethyl acetate, heptane, hexane, methyl t-butyl ether, tetrahydrofuran, and toluene, or a mixture of two or more thereof. Preferably the solvent is t-butyl alcohol.

In certain embodiments, step (b-2) occurs in the presence of a suitable base, such as, but not limited to, triethylamine, diisopropylethylamine, or N-methylmorpholine. A preferred base is triethylamine.

In certain embodiments, step (b-2) occurs in the presence of a suitable Curtis rearrangement agent, such as, but not limited to, diphenylphosphoryl azide, trimethylsilyl azide, sodium azide, iodine azide. Preferably the Curtis rearrangement agent is diphenylphosphoryl azide.

In one embodiment, the reaction is conducted at a temperature from about 0° C. to about 100° C., preferably from about 60° C. to about 90° C., and more preferably about 85° C. In one embodiment, step (b-2) takes place for a period from about 1 hour to about 1 day, preferably about 1 day to about 10 hours, and more preferably about 2 hours.

In a preferred embodiment, the process of the invention further comprises isolating Compound (m), preferably in a substantially pure form.

Step (b-3)

In preferred embodiments, step (b-3) occurs in a in a solvent. Suitable solvents include, but are not limited to, dichloromethane, chloroform, dioxane, ethyl acetate, heptane, hexane, methyl t-butyl ether, tetrahydrofuran, and toluene, or a mixture of two or more thereof. Preferably the solvent is tetrahydrofuran.

In certain embodiments, step (b-3) occurs in the presence of a suitable base, such as, but not limited to, n-butyllithium, isobutyllithium, t-butyllithium, lithium diisopropyl amide, lithium tetramethylpiperidide, sodium diisopropyl amide, lithium bis(trimethylsilyl)amide, sodium bis(trimethylsilyl)amide, potassium bis(trimethylsilyl)amide, or the like. A preferred base is n-butyllithium.

In certain embodiments, the protecting reagent in step (b-3) is such as, but not limited to, chloromethylsilane, hexamethylsilazane, bis(trimethylsilyl)acetamide, bis(trimethylsilyl(trifluoroacetamide, dimethylaminotrimethylsilane, N-trimethylsilylimidazole, trimethylsilyltriflate, or the like. A preferred base is chloromethylsilane.

In certain embodiments, protecting reagent in step (b-3) is a chlorination reagent is such as, but not limited to, hexachloroethane, or the like. A preferred base is hexachloroethane.

In one embodiment, the reaction is conducted at a temperature from about −100° C. to about −40° C., preferably from about −90° C. to about −60° C., and more preferably about −80° C. In one embodiment, step (b-3) takes place for a period from about 30 minutes to about 10 hours, preferably about 30 minutes to about 3 hours, and more preferably about 1 hour.

In a preferred embodiment, the process of the invention further comprises isolating the compound of Formula (N), preferably in a substantially pure form.

Step (b-4)

In preferred embodiments, step (b-4) occurs in a in a solvent. Suitable solvents include, but are not limited to, dichloromethane, chloroform, dioxane, ethyl acetate, heptane, hexane, methyl t-butyl ether, tetrahydrofuran, and toluene, or a mixture of two or more thereof. Preferably the solvent is tetrahydrofuran.

In certain embodiments, step (b-4) occurs in the presence of a suitable base, such as, but not limited to, n-butyllithium, isobutyllithium, t-butyllithium, lithium diisopropyl amide, lithium tetramethylpiperidide, sodium diisopropyl amide, lithium bis(trimethylsilyl)amide, sodium bis(trimethylsilyl)amide, potassium bis(trimethylsilyl)amide, or the like. A preferred base is n-butyllithium.

In certain embodiments, the formylation reagent is such as, but not limited to, N,N-dimethylformamide, N-phenyl-N-methylformamide, or the like. A preferred base is N,N-dimethylformamide.

In one embodiment, the reaction is conducted at a temperature from about −100° C. to about −40° C., preferably from about −90° C. to about −60° C., and more preferably about −80° C. In one embodiment, step (b-4) takes place for a period from about 30 minutes to about 10 hours, preferably about 30 minutes to about 3 hours, and more preferably about 1.5 hour.

In a preferred embodiment, the process of the invention further comprises isolating the compounds of Formula (P), preferably in a substantially pure form.

Step (b-5)

In preferred embodiments, step (b-5) occurs in a solvent. Suitable solvents include, but are not limited to, dichloromethane, chloroform, dioxane, ethyl acetate, heptane, hexane, methyl t-butyl ether, tetrahydrofuran, and toluene, or a mixture of two or more thereof. Preferably the solvent is tetrahydrofuran.

In certain embodiments, step (b-5) occurs in the presence of a suitable base, such as, but not limited to, n-butyllithium, isobutyllithium, t-butyllithium, lithium diisopropyl amide, lithium tetramethylpiperidide, sodium diisopropyl amide, lithium bis(trimethylsilyl)amide, sodium bis(trimethylsilyl)

amide, potassium bis(trimethylsilyl)amide, or the like. A preferred base is lithium bis(trimethylsilyl)amide.

In certain embodiments, Step (b-5) is carried out at a suitable temperature, such as for example from about −20° C. to about 50° C., preferably from about −10° C. to about 20° C., and more preferably about 0° C. In one embodiment, step (b-5) takes place for a period from about 30 minutes to about 10 hours, preferably about 1 hour.

In preferred embodiments, the process of the invention further includes isolating the compound of Formula (Q), preferably in substantially pure form.

Step (b-6)

In preferred embodiments, step (b-6) occurs in a solvent. Suitable solvents include, but are not limited to, methanol, ethanol, acetonitrile, dichloromethane, chloroform, dioxane, ethyl acetate, heptane, hexane, methyl t-butyl ether, tetrahydrofuran, and toluene, or a mixture of two or more thereof. Preferably the solvent is ethanol.

In certain embodiments, step (b-6) occurs in the presence of a suitable acid, such as, but not limited to, hydrochloride acid, phosphonic acid, sulfuric acid, trifluoroacetic acid, p-toluenesulfonic acid, or the like. A preferred acid is hydrochloride acid.

In certain embodiments, Step (b-6) is carried out at a suitable temperature, such as for example from about 50° C. to about 100° C., preferably from about 70° C. to about 90° C., and more preferably about 80° C. In one embodiment, step (b-6) takes place for a period from about 1 hour to about 20 hours, preferably about 6 hours.

In preferred embodiments, the process of the invention further includes isolating the compound of Formula (R), preferably in substantially pure form.

Step (b-7a)

In preferred embodiments, step (b-7a) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, and toluene, and mixtures of two or more thereof. A preferred solvent is methanol.

In certain embodiments, step (b-7a) occurs in the presence of a catalyst. Suitable catalysts include, but are not limited to, palladium on carbon, palladium hydroxide on carbon, or Raney nickel. Preferably the catalyst is palladium on carbon.

In certain embodiments, step (b-7a) is carried out at a suitable hydrogen pressure, such as, but not limited to, from about 0.5 atm to about 3 atm, preferably about 1 atm.

Step (b-7a) is carried out at a suitable temperature, such as, for example, from about 0° C. to about 100° C., preferably about 15° C. to about 25° C. In one embodiment, step (b-7a), the reaction takes place over a period from about 24 hours to about 10 days, preferably about 7 days.

In preferred embodiments, the process of the invention further comprises isolating Compound (R-1), preferably in substantially pure form.

Step (b-7)

Step (b-7) preferably occurs in the presence of a solvent. Suitable solvents include acetonitrile, acetone, dichloromethane, dimethyl formamide, dimethyl sulfoxide, dioxane, heptane, hexane, methanol, methyl t-butyl ether, tetrahydrofuran, water, and toluene, or a mixture of two or more thereof, optionally in the present of a co-solvent. Preferably the solvent is methyl t-butyl ether. More preferably the solvent is tetrahydrofuran and the co-solvent is water. Preferably the volume ratio of tetrahydrofuran to water is about 2:5.

In certain embodiments, step (b-7) occurs in the presence of a base to hydrolyze the $C_1$-$C_4$-alkyl ester, preferably a methyl or ethyl ester. Suitable bases include, but are not limited to, sodium hydroxide, potassium hydroxide, lithium hydroxide, and combinations of two or more thereof. A preferred base is sodium hydroxide. After the saponification reaction, Compound (1) is formed by treatment with an acid, such as, but not limited to, hydrogen chloride, hydrogen bromide, sulfuric acid or a combination of two or more thereof. A preferred acid is hydrogen chloride.

Step (b-7) is carried out at a suitable temperature, such as, for example, from about 30° C. to about 100° C., preferably from about 55° C. to about 65° C. In one embodiment, the invention relates to step (b-7), the reaction takes place over a period from about 1 hour to about 3 days, preferably from about 10 hours to about 48 hours, and more preferably about 24 hours.

Preferably, the process of the invention further comprises isolating Compound (1), preferably in substantially pure form.

In another embodiment, the present invention provides a process for the preparation of Compound (1)

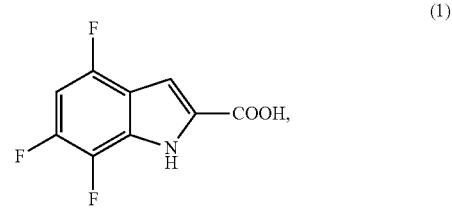

the process comprising the steps of:

(c-1) reacting Compound (r) with a bromination agent to produce Compound (s), 2-bromo-3,4,6-trifluoroaniline:

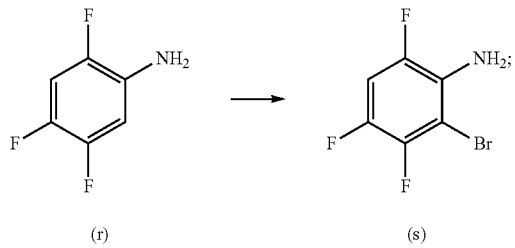

(c-2) reacting Compound (s) with a diazotization agent to produce Compound (t-Int), 2-bromo-3,4,6-trifluorobenzo diazonium salt:

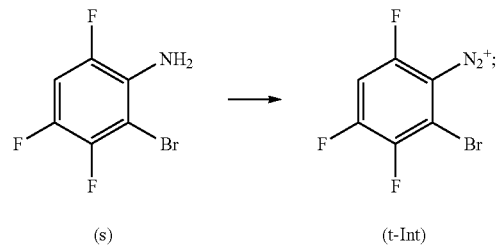

(c-3) reacting Compound (t-Int) with a cyanation agent to produce Compound (t), 2-bromo-3,4,6-trifluorobenzonitrile:

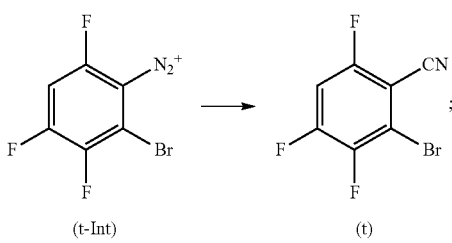

(c-4) reacting Compound (t) with a reducing agent to produce Compound (u), 2-bromo-3,4,6-trifluorobenzaldehyde:

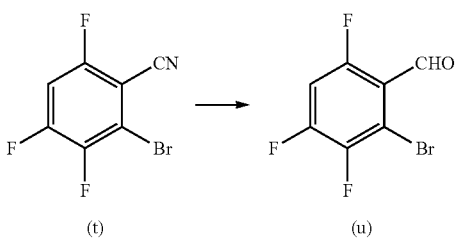 [SMILES: N#Cc1c(F)cc(F)c(F)c1Br ; O=Cc1c(F)cc(F)c(F)c1Br]

(c-5) reacting Compound (u) with the compound of Formula (D-1) to produce the compound of Formula (V):

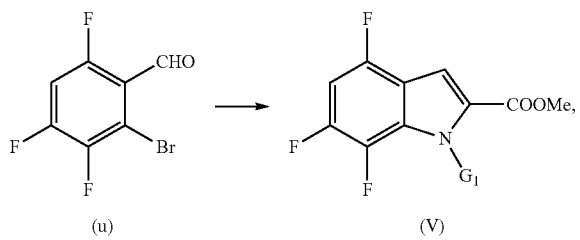

wherein $G_1$ is previously defined; and (c-6) hydrolyzing compound of Formula (V) to produce Compound (1):

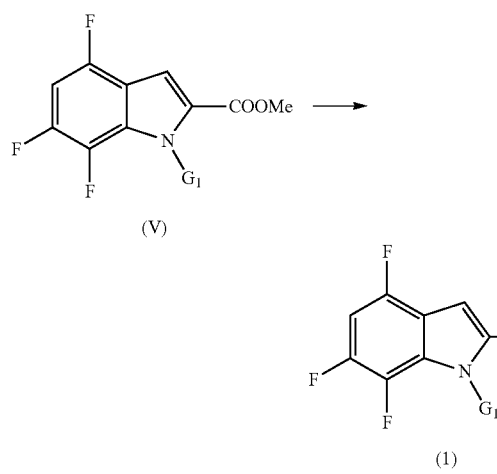

Step (c-1)

In preferred embodiments, step (c-1) occurs in a solvent. Suitable solvents include, but are not limited to, sulfuric acid, acetic acid, or trifluoroacetic acid, trifluoromethyl sulfonic acid, acetonitrile, acetone, chloroform, dichloromethane, dimethyl formamide, dimethyl sulfoxide, dioxane, ethyl acetate, heptane, hexane, methanol, methyl t-butyl ether, tetrachloromethane, tetrahydrofuran, and toluene, or a mixture of two or more thereof. Preferably the solvent is acetic acid.

In certain embodiments, the bromination agent is such as, but not limited to, bromine, bromine trifluoride, N-bromoacetamide, 1,3-dibromo-5,5-dimethylhydantoin (dibromantin or DBH or DBDMH), 1-bromopyrrolidine-2,5-dione (N-bromosuccinimide; 1-NBS)), N-bromosaccharin (NBSac), 2,2-dibromo-2-cyano-acetamide, 5,5-dibromo-2,2-dimethyl-4,6-dioxo-1,3-dioxane, monopyridin-1-ium tribromide ($PyHBr_3$), sodium monobromoisocyanurate, tetrabromomethane, tribromoisocyanuric acid, or the like. The bromination agent is preferably bromine.

In one embodiment, the reaction is conducted at a temperature from about 0° C. to about 100° C., preferably from about 0° C. to about 40° C., and more preferably about 20° C. In one embodiment, step (c-1) takes place for a period from about 1 hour to about 3 days, preferably about 10 hours to about 24 hours, and more preferably about 17 hours.

In a preferred embodiment, the process of the invention further comprises isolating Compound (s), preferably in a substantially pure form.

Step (c-2)

In preferred embodiments of step (c-2), the diazotization occurs in a solvent. Suitable solvents include, but are not limited to, sulfuric acid, acetic acid, trifluoromethyl sulfonic acid, acetonitrile, acetone, chloroform, dichloromethane, dimethyl formamide, dimethyl sulfoxide, dioxane, ethyl acetate, heptane, hexane, methanol, methyl t-butyl ether, tetrachloromethane, tetrahydrofuran, water, and toluene, or a mixture of two or more thereof. Preferably the solvent is 6 N sulfuric acid with water as co-solvent. Preferably the volume ratio of 6 N sulfuric acid to water is about 3:1.

In certain embodiments, the diazotization agent is such as, but not limited to, sodium nitrite, potassium nitrite, tert-butyl nitrite, or the like. The diazotization agent is preferably sodium nitrite.

In one embodiment, the reaction is conducted at a temperature from about –20° C. to about 50° C., preferably from about –10° C. to about 10° C., and more preferably about 0° C. In one embodiment, diazotization takes place for a period from about 30 minutes to about 24 hours, preferably about 30 minutes to about 3 hours, and more preferably about 1 hour.

In a preferred embodiment of step (c-2), the Compound (t-Int) is not isolated and is directly converted to next step.

Step (c-3)

In preferred embodiments of step (c-3), the cyanation occurs in a solvent. Suitable solvents include, but are not limited to, acetonitrile, acetone, chloroform, dichloromethane, dimethyl formamide, dimethyl sulfoxide, dioxane, ethyl acetate, heptane, hexane, methanol, methyl t-butyl ether, tetrachloromethane, tetrahydrofuran, water, and toluene, or a mixture of two or more thereof. Preferably the solvent is toluene with water as co-solvent. Preferably the volume ratio of toluene to water is about 1:5.

In certain embodiments, the cyanation agent is such as, but not limited to, sodium cyanide, potassium cyanide, cupper cyanide, trimethylsilyl cyanide, potassium hexacyanoferrate (II), or the like. The cyanation agent is preferably sodium cyanide.

In certain embodiments, the cyanation occurs in the presence of a catalyst. Suitable catalysts include, but are not limited to, copper (II) chloride, copper (II) bromide, copper (I) iodide, copper (II) sulfate, copper (I) cyanide, copper (I) oxide, or the like. Preferably the catalyst is copper (II) sulfate.

In certain embodiments, the cyanation occurs in the presence of a base. Suitable bases include, but are not limited to, sodium carbonate, sodium bicarbonate, sodium hydroxide, sodium phosphonate dibasic, sodium phosphate tribasic, sodium phosphate dibasic, sodium acetate, sodium citrate, potassium carbonate, potassium bicarbonate, potassium hydroxide, potassium phosphonate dibasic, potassium phosphate tribasic, potassium phosphate dibasic, potassium acetate, potassium citrate, lithium carbonate, lithium bicarbonate, lithium hydroxide, lithium phosphonate dibasic, lithium phosphate tribasic, lithium phosphate dibasic, lithium acetate, lithium citrate, cesium sodium carbonate, cesium bicarbonate, cesium hydroxide, cesium phosphonate dibasic, cesium phosphate tribasic, cesium phosphate dibasic, cesium acetate, cesium citrate, triethylamine, di-isopropylethylamine, N-methylmorpholine, or a combination of two or more thereof. Preferably the base is sodium bicarbonate.

In one embodiment, the reaction is conducted at a temperature from about 20° C. to about 100° C., preferably from about 40° C. to about 60° C., and more preferably about 60° C. In one embodiment, cyanation takes place for a period from about 10 minutes to about 24 hours, preferably about 1 hour, and more preferably about 30 minutes.

In a preferred embodiment, the process of the invention further comprises isolating Compound (t), preferably in a substantially pure form.

Step (c-4)

In preferred embodiments, step (c-4) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and a mixture of two or more thereof. A preferred solvent is dichloromethane.

In preferred embodiments of step (c-4), the reducing agent can be any suitable reducing agent, such as diisobutylaluminum hydride, lithium triethoxyaluminohydride, tin (II) chloride, Raney Nickel, or the like. A preferred reducing agent is diisobutylalumnium hydride.

Compound (u) is formed by treatment of the reduction product with an acid, such as, but not limited to, hydrogen chloride, hydrogen bromide, sulfuric acid, citric acid or a combination of two or more thereof. A preferred acid is citric acid.

In preferred embodiments, step (c-4) is carried out at a suitable temperature, such as, for example, from about −80° C. to about 0° C., preferably from about −50° C. to about −30° C., more preferably about −40° C. In certain embodiments, step (c-4) takes place for a period from about 1 hour to about 24 hours, preferably about 3.5 hours.

In preferred embodiments, the process of the invention further comprises isolating Compound (u), preferably in a substantially pure form.

Step (c-5)

In preferred embodiments, step (c-5) occurs in a solvent. Suitable solvents include, but are not limited to, acetonitrile, acetone, dichloromethane, dichloroethane, dimethyl formamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. A preferred solvent is dichloromethane.

In certain embodiments, step (c-5) occurs in the presence of a catalyst. Suitable catalysts include, but are not limited to, cuprous iodide, copper (I) oxide, copper(I) thiophene-2-carboxylate, and [1,1'-bis(diphenylphosphino)ferrocene] palladium (II) dichloride, optionally in the presence of a ligand, such as, but not limited to, 2,2'-bipyridine, 1,10-phenanthroline, or (S)-proline.

In certain embodiments, step (c-5) occurs in the presence of a suitable base. Suitable bases include, but are not limited to, sodium carbonate, sodium bicarbonate, sodium hydroxide, sodium phosphonate dibasic, sodium phosphate tribasic, sodium phosphate dibasic, sodium acetate, sodium citrate, potassium carbonate, potassium bicarbonate, potassium hydroxide, potassium phosphonate dibasic, potassium phosphate tribasic, potassium phosphate dibasic, potassium acetate, potassium citrate, lithium carbonate, lithium bicarbonate, lithium hydroxide, lithium phosphonate dibasic, lithium phosphate tribasic, lithium phosphate dibasic, lithium acetate, lithium citrate, cesium sodium carbonate, cesium bicarbonate, cesium hydroxide, cesium phosphonate dibasic, cesium phosphate tribasic, cesium phosphate dibasic, cesium acetate, cesium citrate, triethylamine, di-isopropylethylamine, N-methylmorpholine, or a combination of two or more thereof. Preferably the base is potassium phosphate tribasic.

In certain embodiments, step (c-5) occurs in the presence of a catalyst, a ligand, and a base. Preferably the catalyst is cuprous iodide, the ligand is 2,2'-bipyridine or 1,10-phenanthroline, and the base is potassium phosphate tribasic. Preferably the molar ratio of cuprous iodide and 2,2'-bipyridine or 1,10-phenanthroline is about 1:1.

In certain embodiments, step (c-5) is carried out at a suitable temperature, such as for example from about 0° C. to about 100° C., preferably from about 0° C. to about 40° C., and more preferably about 25° C. In one embodiment, step (c-5) takes place for a period from about 10 hours to about 24 hours, preferably about 16 hours.

In preferred embodiments, the process of the invention further includes isolating the compound of Formula (V), preferably in substantially pure form.

Step (c-6)

In certain embodiments, step (c-6) preferably occurs in the presence of a solvent. Suitable solvents include acetonitrile, acetone, dichloromethane, dimethyl formamide, dimethyl sulfoxide, dioxane, heptane, hexane, methanol, methyl t-butyl ether, tetrahydrofuran, water, and toluene, or a mixture of two or more thereof, optionally in the present of a co-solvent. Preferably the solvent is methyl t-butyl ether. More preferably the solvent is tetrahydrofuran, and the co-solvent is water. Preferably the volume ratio of tetrahydrofuran to water is about 2:5.

In certain embodiments, step (c-6) occurs in the presence of a base to remove the -$G_1$ group and hydrolyze the methyl ester. Suitable bases include, but are not limited to, sodium hydroxide, potassium hydroxide, lithium hydroxide, and combinations of two or more thereof. A preferred base is sodium hydroxide. After the saponification reaction, Compound (1) is formed by treatment with an acid, such as, but not limited to, hydrogen chloride, hydrogen bromide, sulfuric acid or a combination of two or more thereof. A preferred acid is hydrogen chloride.

In certain embodiments, step (c-6) is carried out at a suitable temperature, such as, for example, from about 30° C. to about 100° C., preferably from about 55° C. to about 65° C. In one embodiment, the invention relates to step (c-6), the reaction takes place over a period from about 1 hours to about 3 days, preferably about 24 hours.

Preferably, the process of the invention further comprises isolating Compound (1), preferably in a substantially pure form.

In one embodiment, the present invention provides a process for the preparation of Compound (1)

(1)

the process comprises the steps of:

(1) reacting Compound (a), 2,4,5-trifluorobenzoic acid, with a bromination agent, to produce Compound (b):

(a) → (b)

(2) reacting Compound (b) with an acid activation reagent followed by a reducing agent to produce Compound (c-1), (2,5-dibromo-3,4,6-trifluorophenyl) methanol:

(b) → (c-1)

(3) reacting Compound (c-1) with an oxidizing agent to produce Compound (d), 2,5-dibromo-3,4,6-trifluorobenzaldehyde:

(c-1) → (d)

(4) reacting Compound (d) with compound of Formula (D-2)

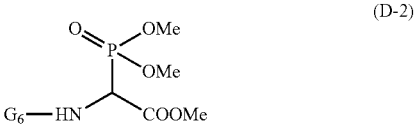
(D-2)

to yield a compound of Formula (E):

(d) 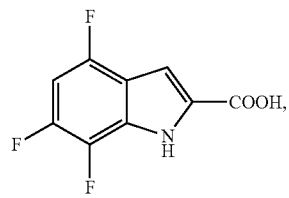 (D-2) →

(E)

wherein $G_6$ is -Cbz, -Fmoc, -Moz, or -Pnz; preferably $G_6$ is -Cbz;

(5) hydrolyzing the compound of Formula (E) to produce the Compound (g):

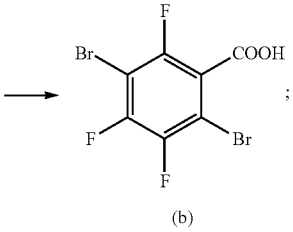 →

(E)

(g)

and (6) reacting Compound (g) with a hydrogen source, such as $H_2$, ammonium formate, or cyclohexa-1,4-diene in the presence of hydrogenation catalysts, to produce Compound (1):

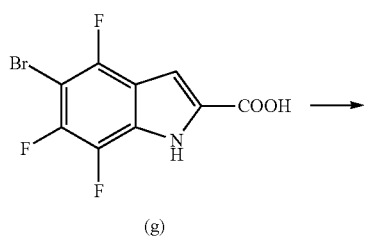

(g)

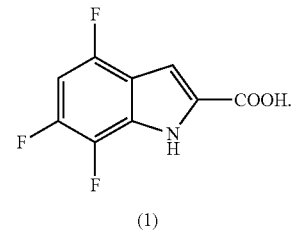

(1)

Step (1)

In preferred embodiments, step (1) occurs in a solvent. Suitable solvents include, but are not limited to, sulfuric acid, acetic acid, trifluoromethyl sulfonic acid, acetonitrile, acetone, chloroform, dichloromethane, dimethyl formamide, dimethyl sulfoxide, dioxane, ethyl acetate, heptane, hexane, methanol, methyl t-butyl ether, tetrachloromethane, tetrahydrofuran, and toluene, or a mixture of two or more thereof. Preferably the solvent is sulfuric acid.

In certain embodiments, the bromination agent is bromine, bromine trifluoride, N-bromoacetamide, 1,3-dibromo-5,5-dimethylhydantoin (dibromantin or DBH or DBDMH), 1-bromopyrrolidine-2,5-dione (N-bromosuccinimide; 1-NBS)), N-bromosaccharin (NBSac), 2,2-dibromo-2-cyano-acetamide, 5,5-dibromo-2,2-dimethyl-4,6-dioxo-1,3-dioxane, monopyridin-1-ium tribromide (PyHBr$_3$), sodium monobromoisocyanurate, tetrabromomethane, tribromoisocyanuric acid, or the like. The bromination agent is preferably 1,3-dibromo-5,5-dimethylhydantoin.

In one embodiment, the reaction is conducted at a temperature from about −20° C. to about 20° C., preferably from about −5° C. to about 5° C. In one embodiment, the reaction takes place over a period from about 15 hours to about 36 hours, preferably about 28 hours.

In a preferred embodiment, the process of the invention further comprises isolating Compound (b), preferably in a substantially pure form.

Step (2)

In preferred embodiments, the acid activation in step (2) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and a mixture of two or more thereof. A preferred solvent in acid activation is dichloromethane.

The acid activation reagent can be any suitable agent, such as, but not limited to, oxalyl chloride, sulfonyl chloride, 1-Chloro-N,N,2-trimethyl-1-propenylamine, isobutyl chloroformate, isopropyl chloroformate, hydroxybenzotriazole (HOBt), or the like. A preferred acid activation reagent is a suitable acid chloride formation reagent, such as oxalyl chloride, sulfonyl chloride, 1-chloro-N,N,2-trimethyl-1-propenylamine, or the like. More preferred acid activation reagent is oxalyl chloride.

The acid activation in step (2) is carried out at a suitable temperature, such as, for example, from about 0° C. to about 100° C., preferably from about 0° C. to about 50° C., more preferably about 25° C. In certain embodiments, acid activation in step (2) takes place for a period from about 1 hour to about 24 hours, preferably about 1.5 hours.

In preferred embodiments, the reduction in step (2) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and a mixture of two or more thereof. A preferred solvent is tetrahydrofuran.

The reducing agent can be any suitable reducing agent, such as but not limited to lithium aluminum hydride, lithium borohydride, sodium borohydride, diisobutylaluminum hydride, borane-tetrahydrofuran complex, borane-dimethyl sulfide complex, or the like. Preferably the reducing agent is lithium borohydride.

The reduction in step (2) is carried out at a suitable temperature, such as, for example, from about −20° C. to about 30° C., preferably from about −10° C. to about 10° C., more preferably about 0° C. In certain embodiments, the reduction in step (2) takes place for a period from about 30 minutes to about 5 hours, preferably about 1 hour.

In preferred embodiments, the process of the invention further comprises isolating Compound (c-1), preferably in a substantially pure form.

Step (3)

In preferred embodiments, step (3) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and a mixture of two or more thereof. A preferred solvent is dichloromethane.

In one embodiment, the oxidizing agent can be, but is not limited to, trichloroisocyanuric acid with TEMPO, sodium hypochlorite with TEMPO, oxalyl chloride with dimethyl sulfoxide, manganese oxide, chromiumtrioxide, pyridinium chlorochromate, sodium perchloride, Dess-Martin periodinane, or the like. A preferred oxidizing agent is trichloroisocyanuric acid with TEMPO.

In one embodiment, step (3) is conducted at a temperature from about −20° C. to about 50° C., preferably from about −10° C. to about 10° C., and more preferably about 0° C. In certain embodiments, step (3) takes place for a period from about 10 minutes to about 10 hours, preferably about 30 minutes.

In preferred embodiments, the process of the invention further comprises isolating Compound (d), preferably in a substantially pure form.

Step (4)

In preferred embodiments, step (4) occurs in a solvent. Suitable solvents include, but are not limited to, acetonitrile, acetone, dichloromethane, dichloroethane, dimethyl formamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. A preferred solvent is dichloromethane.

In certain embodiments, step (4) occurs in the presence of a catalyst. Suitable catalysts include, but are not limited to, cuprous iodide, copper (I) oxide, copper(I) thiophene-2-carboxylate, and [1,1'-bis(diphenylphosphino)ferrocene] palladium (II) dichloride, optionally in the presence of a ligand, such as, but not limited to, 2,2'-bipyridine, 1,10-phenanthroline, or (S)-proline.

In certain embodiments, step (a-1) occurs in the presence of a suitable base. Suitable bases include, but are not limited to, sodium carbonate, sodium bicarbonate, sodium hydroxide, sodium phosphonate dibasic, sodium phosphate tribasic, sodium phosphate dibasic, sodium acetate, sodium citrate, potassium carbonate, potassium bicarbonate, potassium hydroxide, potassium phosphonate dibasic, potassium phosphate tribasic, potassium phosphate dibasic, potassium acetate, potassium citrate, lithium carbonate, lithium bicarbonate, lithium hydroxide, lithium phosphonate dibasic, lithium phosphate tribasic, lithium phosphate dibasic, lithium acetate, lithium citrate, cesium sodium carbonate, cesium bicarbonate, cesium hydroxide, cesium phosphonate dibasic, cesium phosphate tribasic, cesium phosphate dibasic, cesium acetate, cesium citrate, triethylamine, di-isopropylethylamine, N-methylmorpholine, or a combination of two or more thereof. Preferably the base is potassium phosphate tribasic, sodium phosphate tribasic, potassium carbonate, sodium carbonate, cesium carbonate, triethylamine, di-isopropylethylamine, N-methylmorpholine, potassium acetate or a combination of two or more thereof. More preferably the base is potassium phosphate tribasic.

In certain embodiments, step (4) occurs in the presence of a catalyst, a ligand, and a base. Preferably the catalyst is cuprous iodide, the ligand is 2,2'-bipyridine or 1,10-phenanthroline, and the base is potassium phosphate tribasic. Preferably the molar ratio of cuprous iodide and 2,2'-bipyridine or 1,10-phenanthroline is about 1:1.

Step (4) is carried out at a suitable temperature, such as for example, from about 0° C. to about 100° C., preferably from about 0° C. to about 40° C., and more preferably about 25° C. In one embodiment, step (4) takes place for a period from about 10 hours to about 20 hours, preferably about 15 hours.

In preferred embodiments, the process of the invention further includes isolating compound of Formula (E), preferably in a substantially pure form.

Step (5)

Step (5) preferably occurs in the presence of a solvent. Suitable solvents include acetonitrile, acetone, dichloromethane, dimethyl formamide, dimethyl sulfoxide, dioxane, heptane, hexane, methanol, methyl t-butyl ether, tetrahydrofuran, water, and toluene, or a mixture of two or more thereof, optionally in the present of a co-solvent. Preferably the solvent is tetrahydrofuran, and the co-solvent is water. Preferably the volume ratio of tetrahydrofuran to water is about 2:5.

In certain embodiments, step (5) occurs in the presence of a base to remove the -$G_6$ group and to hydrolyze the methyl ester. Suitable bases include, but are not limited to, sodium hydroxide, potassium hydroxide, lithium hydroxide, and combinations of two or more thereof. A preferred base is sodium hydroxide. After the saponification reaction, Compound (g) is formed by treatment with an acid, such as, but not limited to, hydrogen chloride, hydrogen bromide, sulfuric acid or a combination of two or more thereof. A preferred acid is hydrogen chloride.

Step (5) is carried out at a suitable temperature, such as, for example, from about 30° C. to about 100° C., preferably from about 60° C. to about 70° C. In one embodiment, the invention relates to step (5), the reaction takes place over a period from about 1 hours to about 3 days, preferably about 16 hours.

Preferably, the process of the invention further comprises isolating Compound (g), preferably in substantially pure form.

Step (6)

In preferred embodiments, step (6) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, and toluene, and mixtures of two or more thereof. A preferred solvent is ethanol.

In certain embodiments, step (6) occurs in the presence of a catalyst. Suitable catalysts include, but are not limited to, palladium on carbon, palladium hydroxide on carbon, or Raney nickel. Preferably the catalyst is palladium on carbon.

In certain embodiments, step (6) occurs in the presence of a suitable base. Suitable bases include, but are not limited to, sodium carbonate, sodium bicarbonate, sodium hydroxide, sodium phosphonate dibasic, sodium phosphate tribasic, sodium phosphate dibasic, sodium acetate, sodium citrate, potassium carbonate, potassium bicarbonate, potassium hydroxide, potassium phosphonate dibasic, potassium phosphate tribasic, potassium phosphate dibasic, potassium acetate, potassium citrate, lithium carbonate, lithium bicarbonate, lithium hydroxide, lithium phosphonate dibasic, lithium phosphate tribasic, lithium phosphate dibasic, lithium acetate, lithium citrate, cesium sodium carbonate, cesium bicarbonate, cesium hydroxide, cesium phosphonate dibasic, cesium phosphate tribasic, cesium phosphate dibasic, cesium acetate, cesium citrate, triethylamine, di-isopropylethylamine, N-methylmorpholine, or a combination of two or more thereof. Preferably the base is sodium carbonate.

In certain embodiments, step (6) is carried out at a suitable hydrogen pressure, such as, but not limited to, from about 0.5 atm to about 3 atm, preferably about 1 atm.

Step (6) is carried out at a suitable temperature, such as, for example, from about 0° C. to about 100° C., preferably about 20° C. to about 30° C. In one embodiment, step (a-3a), the reaction takes place over a period from about 1 day to about 10 days, preferably about 42 hours.

In preferred embodiments, the process of the invention further comprises isolating Compound (1), preferably in substantially pure form.

Definitions

Listed below are definitions of various terms used to describe this invention. These definitions apply to the terms as they are used throughout this specification and claims, unless otherwise limited in specific instances, either individually or as part of a larger group.

As used herein a compound in "substantially pure form" is a compound having a purity of at least 75% by weight. Preferably a compound in substantially pure form has a purity of at least 80%, 85%, 90%, 95% or 98% by weight.

As used herein, the term "alkoxy" refers to a radical in which an alkyl group having the designated number of carbon atoms is connected to the rest of the molecule via an oxygen atom. Alkoxy groups include $C_1$-$C_{12}$-alkoxy, $C_1$-$C_8$-alkoxy, $C_1$-$C_6$-alkoxy, $C_1$-$C_4$-alkoxy and $C_1$-$C_3$-alkoxy groups. Examples of alkoxy groups includes, but are not limited to, methoxy, ethoxy, n-propoxy, 2-propoxy (isopropoxy) and the higher homologs and isomers. A preferred alkoxy is $C_1$-$C_3$ alkoxy.

The terms "heterocyclic" and "heterocycloalkyl" can be used interchangeably and refer to a non-aromatic ring or a polycyclic ring system, such as a bi- or tri-cyclic fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic or heterocycloalkyl groups may be further substituted. A heterocycloalkyl or heterocyclic group can be C-attached or N-attached where possible.

The term "halo" or halogen" alone or as part of another substituent, as used herein, refers to a fluorine, chlorine, bromine, or iodine atom.

The term "hydrogen" includes hydrogen and deuterium. In addition, the recitation of an element includes all isotopes of that element so long as the resulting compound is pharmaceutically acceptable. In certain embodiments, the isotopes of an element are present at a particular position according to their natural abundance. In other embodiments, one or more isotopes of an element at a particular position are enriched beyond their natural abundance.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including, but not limited to mesylate, tosylate, triflate, p-nitrobenzoate, phosphonate groups.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in P. G. M. Wuts, *Greene's Protective Groups in Organic Synthesis*, 5th edition, John Wiley & Sons, Hoboken, NJ (2014). Examples of hydroxyl protecting groups include, but are not limited to, benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including but not limited to, benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in P. G. M. Wuts, *Greene's Protective Groups in Organic Synthesis,* 5th edition, John Wiley & Sons, Hoboken, NJ (2014). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2$^{nd}$ Ed. Wiley-VCH (1999); P. G. M. Wuts, *Greene's Protective Groups in Organic Synthesis,* 5th edition, John Wiley & Sons, Hoboken, NJ (2014); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

ABBREVIATIONS

Abbreviations which may be used in the descriptions of the scheme and the examples that follow are:
Cbz for benzyloxycarbonyl;
DMAP for dimethylaminopyridine;
DMF for dimethyl formamide;
EtOAc for ethyl acetate;
HPLC for high-pressure liquid chromatography;
MeOH for methanol;
NMM for N-methylmorpholine;
Rp for hydroxyl protecting group;
RT for room temperature;
TEA for triethylamine;
THF for tetrahydrofuran;
TPP or PPh$_3$ for triphenylphosphine;
Boc for t-butoxycarbonyl;
Bz for benzoyl;
BuLi for n-butyllithium
LiHMDS for lithium bis(trimethylsilyl)amide;
Ac for acetyl;
Fmoc for fluorenylmethyloxycarbonyl;
Moz for p-methoxybenzyloxycarbonyl;
Pnz for p-nitrobenzyloxycarbonyl;
Troc for 2,2-trichloroethoxycarbonyl;
Teoc for 2-(trimethylsilyl)ethoxycarbonyl;
Ph for phenyl;
TMS for trimethylsilyl;
TEMPO for 2,2,6,6-tetramethylpiperidine 1-oxyl;
TLC for thin layer chromatography;
TCCA for trichloroisocyanuric acid;
Ac for acetyl;
Bpy for 2,2'-bipyridine;
DCM for dichloromethane;
DPPA for diphenylphosphoryl azide;
DIBAL-H for diisobutylaluminium hydride;
DMSO for dimethyl sulfoxide;
MTBE for methyl tert-butyl ether;
1, 10-phen for 1,10-phenanthroline.

All other abbreviations used herein, which are not specifically delineated above, shall be accorded the meaning which one of ordinary skill in the art would attach.

Synthetic Schemes

In certain embodiments, the invention involves a method of synthesizing the indole acid of Compound (1) via Compound (e) using a non-azide indole formation reaction to form Compound (e) (see Scheme 1). In certain embodiments, the synthesis of Compound (1) via Compound (e) eliminates the need for handling high energy azide intermediate required to form the indole ring. In certain embodiments, the synthesis of Compound (1) via Compound (e) uses a Horner-Wadsworth-Emmons (HWE) reaction followed by copper catalyzed amination to form the indole ring. In certain embodiments, the synthesis of Compound (1) via Compound (e) results in an overall high throughput.

An embodiment of the process of the invention, shown in Scheme 1, utilizes a Horner-Wadsworth-Emmons (HWE) reaction followed by intramolecular copper catalyzed amination as a key step in the synthesis of Compound (1). In this embodiment, the synthesis of Compound (1) begins with bromination of Compound (a). The carboxylic acid Compound (b) is converted to aldehyde Compound (d) as is known in the art to form the Weinreb amide followed by the reduction. The Compound (e) may undergo debromination by hydrogenation to provide Compound (f), which is subjected to tert-butyloxycarbonyl (Boc) deprotection and saponification to yield Compound (1). In certain embodiments, the synthesis of Compound (1) is based on the construction of the key intermediate, Compound (e).

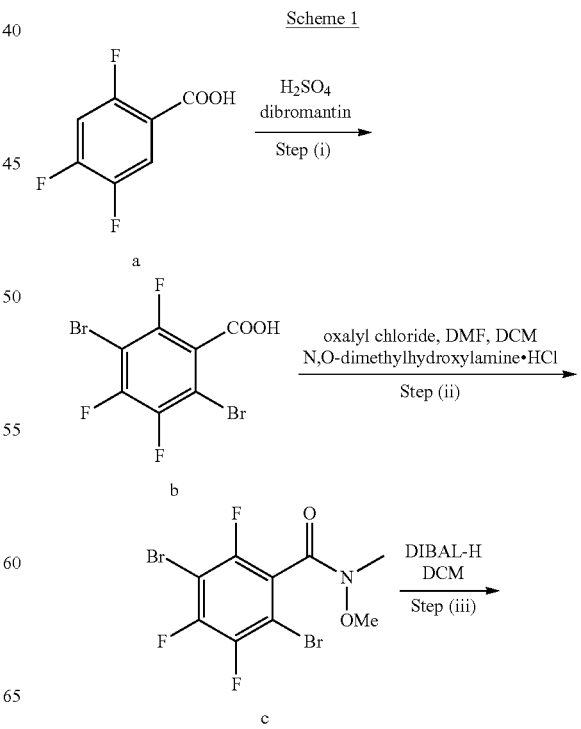

Scheme 1

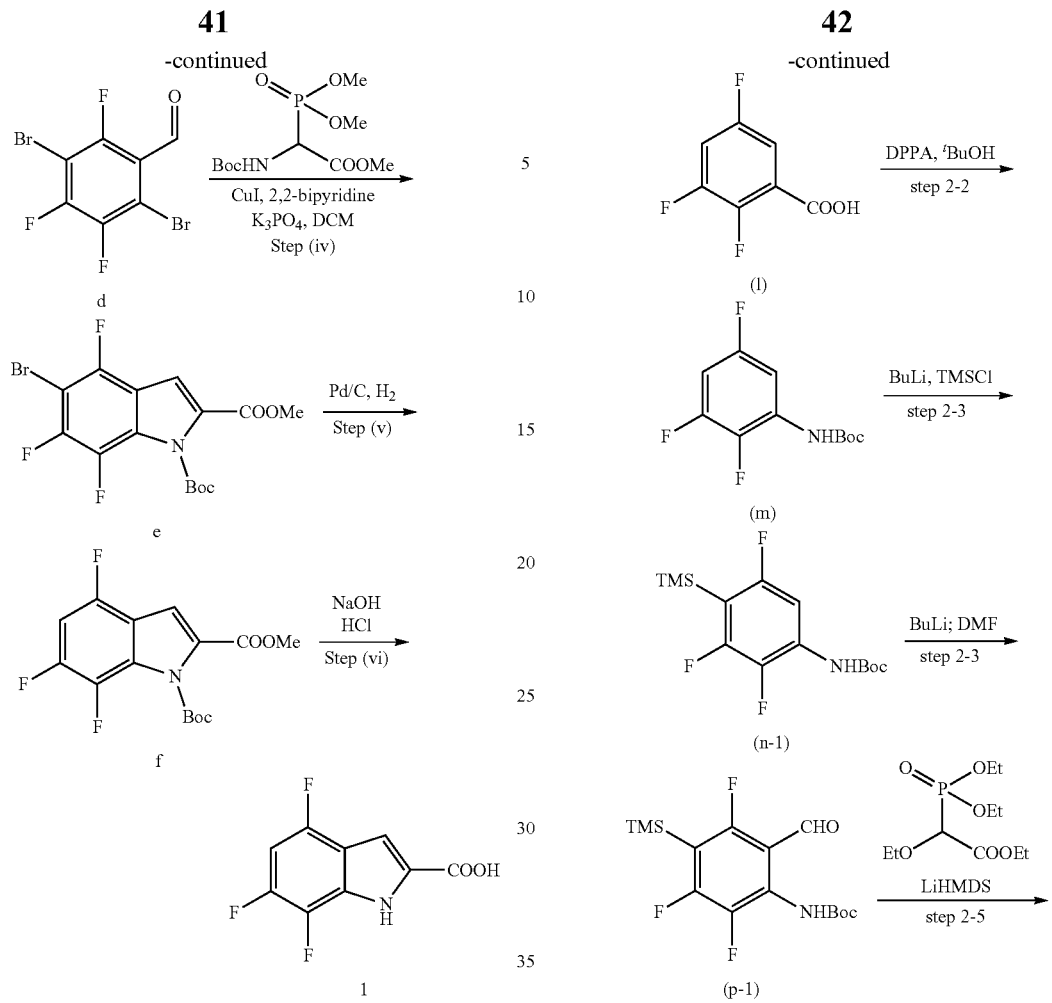

In certain embodiments of the process of the invention, shown in Scheme 2, utilizes a Horner-Wadsworth-Emmons (HWE) reaction followed by intramolecular acid catalyzed ring closure as a key step in the synthesis of Compound (1). In this embodiment, the synthesis of Compound (1) begins with defluorination of Compound (k). The carboxylic acid Compound (1) is converted to protected aniline Compound (m) which is further protected with TMS group as Compound (n-1). The Compound (n-1) may undergo formylation to provide Compound (p-1), which is subjected to Horner-Wadsworth-Emmons (HWE) reaction followed by acid catalyzed ring closure to form Compound (r-1). The Compound (r-1) is then subjected to saponification to yield Compound (1). In certain embodiments, the synthesis of Compound (1) is based on the construction of the key intermediate, Compound (r-1).

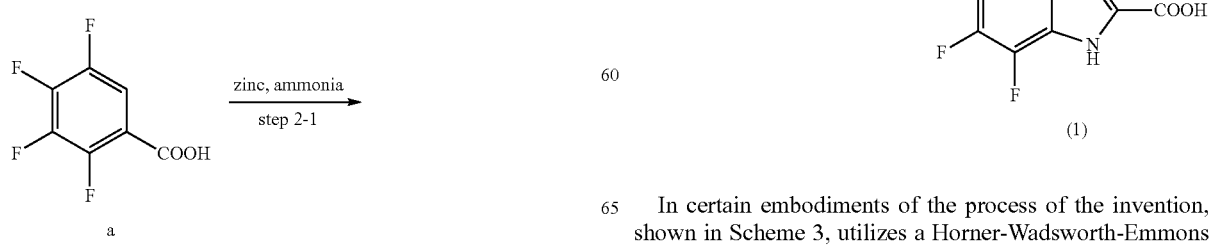

In certain embodiments of the process of the invention, shown in Scheme 3, utilizes a Horner-Wadsworth-Emmons (HWE) reaction followed by intramolecular acid catalyzed ring closure as a key step in the synthesis of Compound (1). In this embodiment, the synthesis of Compound (1) begins with defluorination of Compound (k). The carboxylic acid Compound (1) is converted to protected aniline Compound (m), which is further protected with chloro group as Compound (n-2). Compound (n-2) may undergo formylation to provide Compound (p-2), which is subjected to Horner-Wadsworth-Emmons (HWE) reaction followed by acid catalyzed ring closure to form Compound (r-2). The Compound (r-2) is then subjected to dichlorination and saponification to yield Compound (1). In certain embodiments, the synthesis of Compound (1) is based on the construction of the key intermediate, Compound (r-2).

In certain embodiments of the process of the invention, shown in Scheme 4, utilizes a Horner-Wadsworth-Emmons (HWE) reaction followed by intramolecular acid catalyzed ring closure as a key step in the synthesis of Compound (1). In this embodiment, the synthesis of Compound (1) begins with bromination of Compound (r). The aniline Compound (s) is converted to benzonitrile Compound (t) which is further reduced to provide benzaldehyde Compound (u). The Compound (u) is subjected to Horner-Wadsworth-Emmons (HWE) reaction followed by copper catalyzed ring closure to form Compound (v). The Compound (v) is then subjected to saponification to yield Compound (1). In certain embodiments, the synthesis of Compound (1) is based on the construction of the key intermediate, Compound (v).

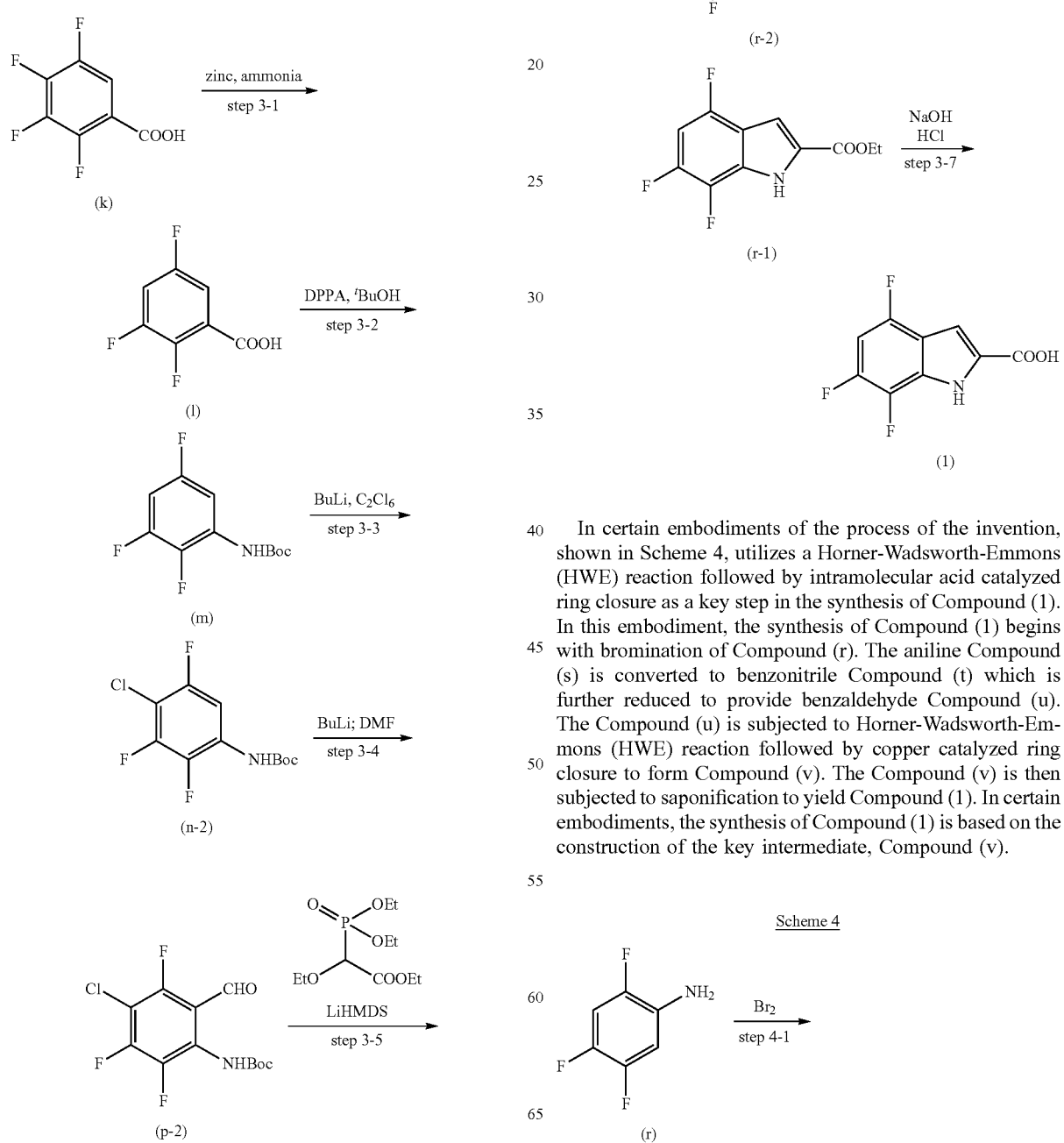

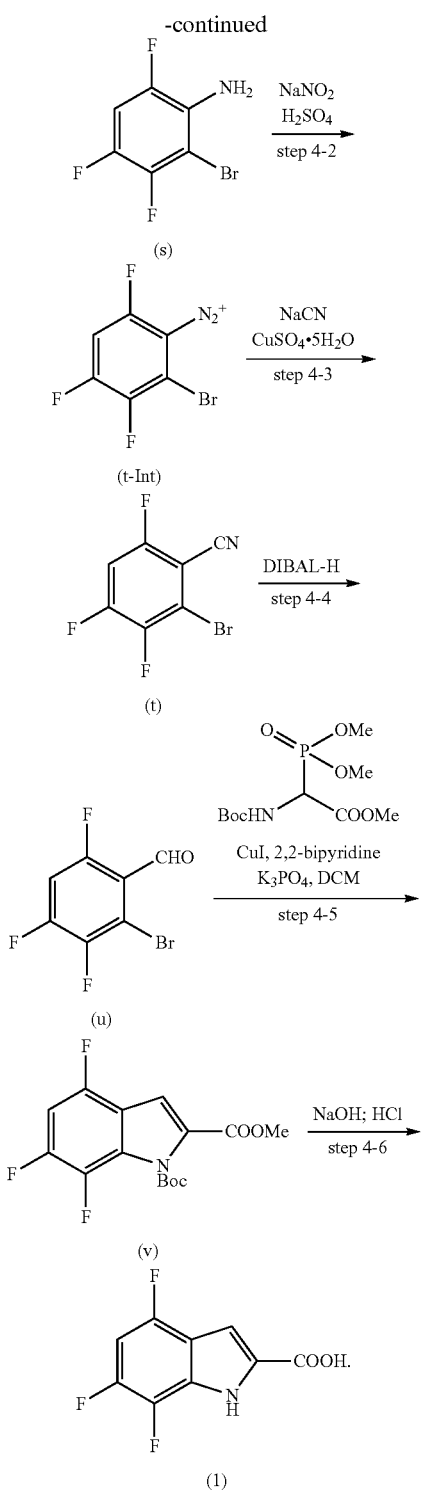

Compound (1). In certain embodiments, the synthesis of Compound (1) is based on the construction of the key intermediate, Compound (i).

Scheme 5

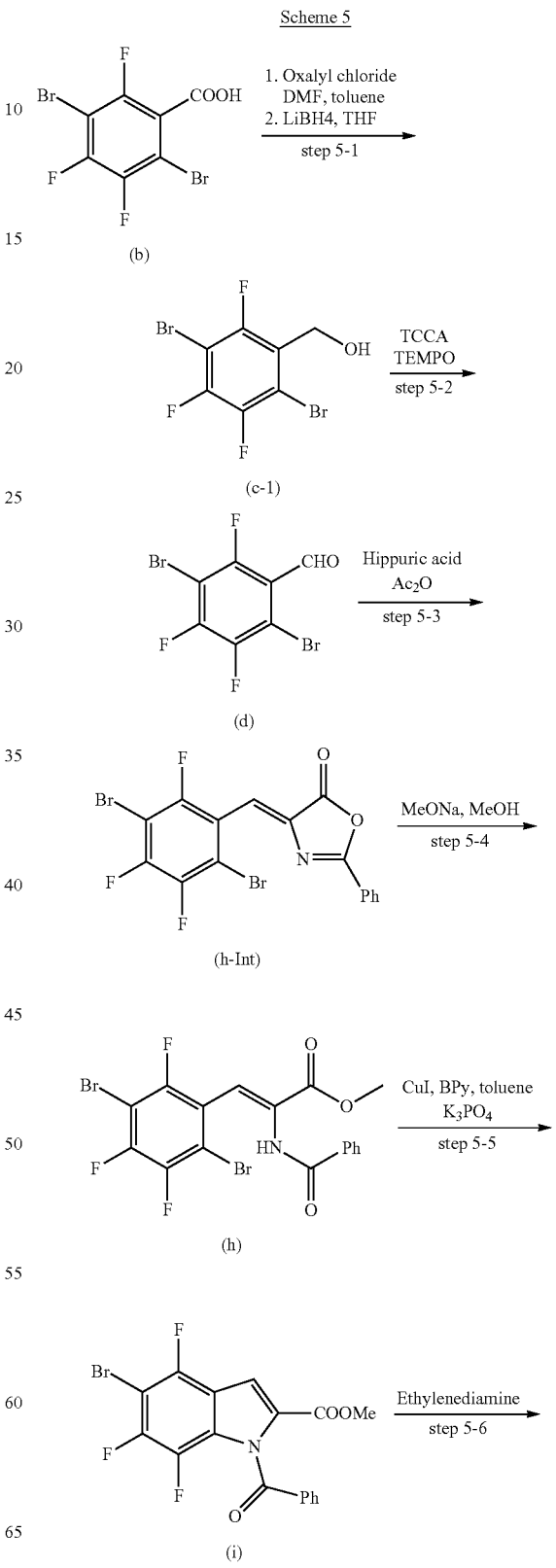

In certain embodiments of the process of the invention, shown in Scheme 5, utilizes a copper catalyzed ring closure as a key step in the synthesis of Compound (1). In this embodiment, the synthesis of Compound (1) begins with reduction of Compound (b) followed by oxidation to provide Compound (d). The benzaldehyde Compound (d) is then condensed with Hippuric acid to provide the key intermediate Compound (h) which is subjected to copper catalyzed ring closure to form Compound (i). The Compound (i) is then subjected to deprotection and saponification to yield

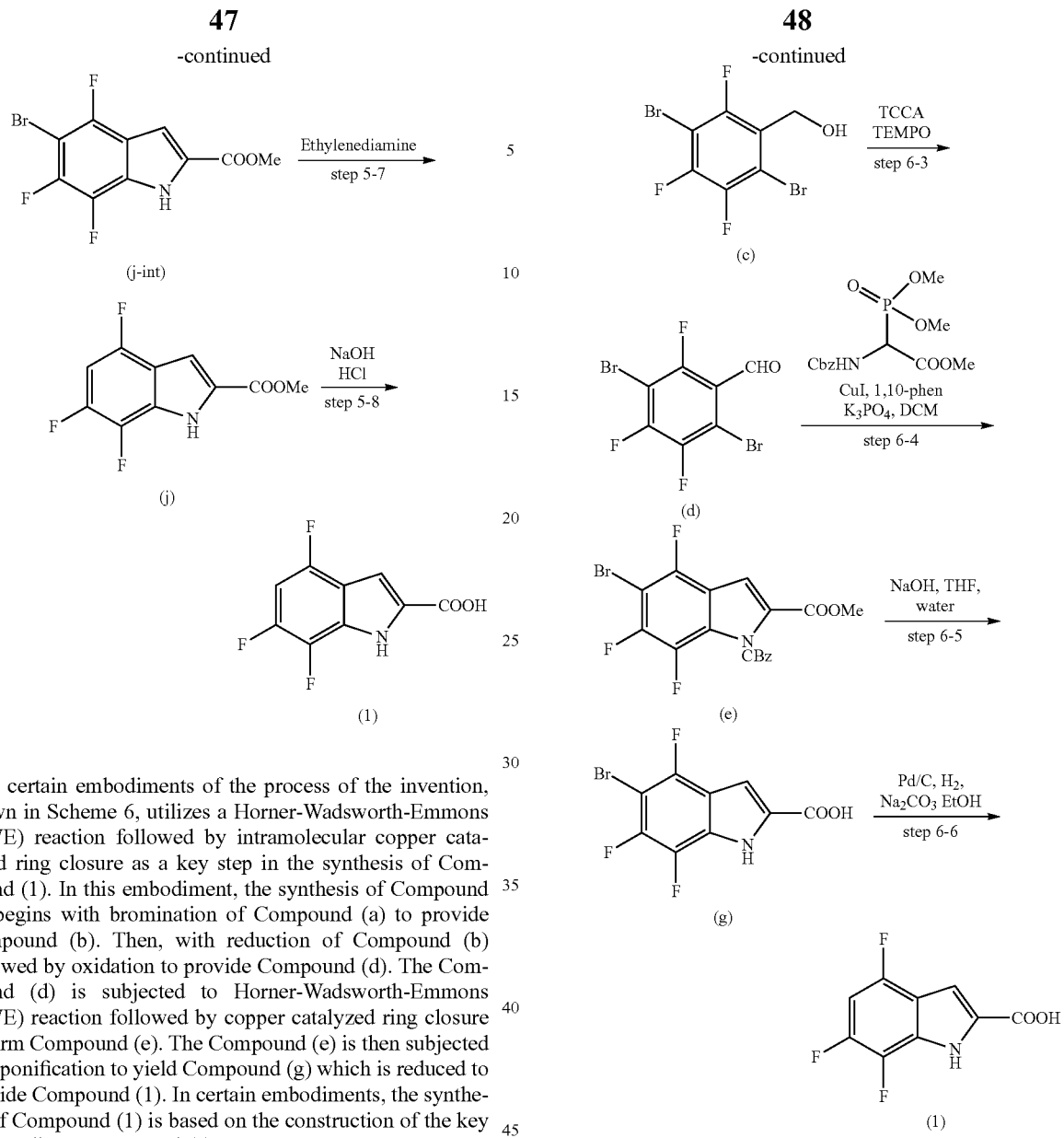

In certain embodiments of the process of the invention, shown in Scheme 6, utilizes a Horner-Wadsworth-Emmons (HWE) reaction followed by intramolecular copper catalyzed ring closure as a key step in the synthesis of Compound (1). In this embodiment, the synthesis of Compound (1) begins with bromination of Compound (a) to provide Compound (b). Then, with reduction of Compound (b) followed by oxidation to provide Compound (d). The Compound (d) is subjected to Horner-Wadsworth-Emmons (HWE) reaction followed by copper catalyzed ring closure to form Compound (e). The Compound (e) is then subjected to saponification to yield Compound (g) which is reduced to provide Compound (1). In certain embodiments, the synthesis of Compound (1) is based on the construction of the key intermediate, Compound (e).

Scheme 6

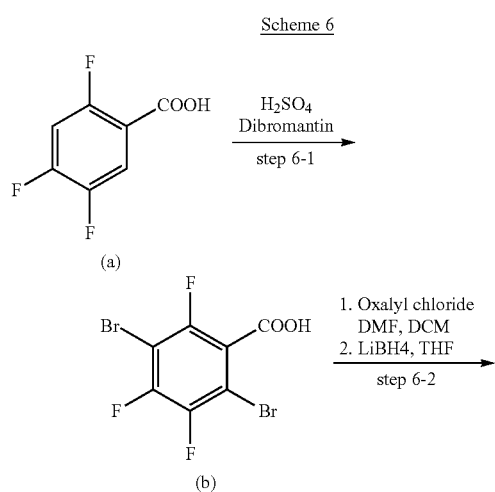

The compounds and processes of the present invention will be understood in connection with the following illustrative methods by which the compounds of the invention may be prepared. It will be understood that any of the reactions described herein, in any of its variations, can be combined with one or more of the other reactions, in any of their respective variations, substantially in analogy with Schemes 1~6 above.

Examples

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1. Preparation of 2,5-dibromo-3,4,6-trifluorobenzoic acid

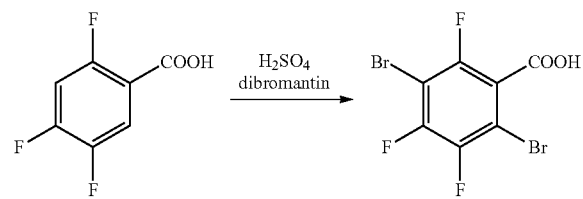 [SMILES: O=C(O)c1cc(F)c(F)cc1F ; O=C(O)c1c(F)c(Br)c(F)c(F)c1Br]

To a flask were added 2,4,5-trifluorobenzoic acid (15 g, 85.2 mmol, 1.00 equiv.), concentrated sulfuric acid (75 mL) and 1,3-dibromo-5,5-dimethylhydantoin (Dibromantin, 53.6 g, 187 mmol, 2.20 equiv.) in 4-5 portions at 0±5° C. The reaction mixture was stirred at the same temperature for 28 hours. The mixture was poured to crushed ice (100 g) with vigorous stirring followed by addition of 5% sodium bicarbonate aqueous solution (45 mL). The precipitated solid was collected by filtration. The wet cake was treated with 5% sodium carbonate aqueous solution to adjust pH to 8-9. The mixture was then extracted with heptane (2×45 mL), and the organic layers were discarded. The aqueous phase was acidified with concentrated hydrochloride acid to pH (~1). The mixture was extracted with ethyl acetate (2×45 mL). After concentration by rotary evaporation, the 2,5-dibromo-3,4,6-trifluorobenzoic acid was obtained as a yellow solid (20 g, 70% yield). $^{19}$F-NMR (282 MHz, DMSO-d$_6$): δ −112.24 (1H), −123.74 (1H), −130.0 (1H).

Example 2. Preparation of 2,5-dibromo-3,4,6-trifluoro-N-methoxy-N-methylbenzamide

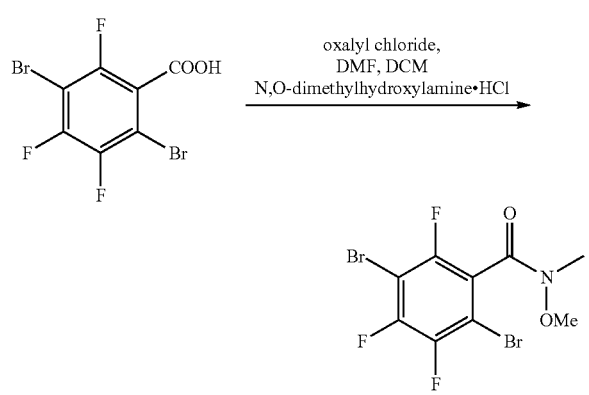

To flask A containing a solution of 2,5-dibromo-3,4,6-trifluorobenzoic acid (12.4 g, 37.1 mmol, 1.00 equiv.) in dichloromethane (62 mL) was added oxalyl chloride (5.6 g, 44.5 mmol, 1.20 equiv.) dropwise at ambient temperature followed by addition of one drop of dimethyl formamide. The reaction mixture was stirred at ambient temperature for 2 hours when the reaction was deemed complete. The prepared benzoyl chloride solution was added dropwise to flask B containing a mixture of dimethylhydroxyamine hydrochloride (4.4 g, 44.5 mmol, 1.20 equiv.) and triethylamine (9.4 g, 92.7 mmol, 2.50 equiv.) in dichloromethane (62 mL) at 0±5° C. After stirring at 0±5° C. for 1 hour, the mixture was washed sequentially with 5% citric acid aqueous solution (36 mL) and 5% sodium bicarbonate aqueous solution (36 mL). The organic layer was separated and concentrated to provide 2,5-dibromo-3,4,6-trifluoro-N-methoxy-N-methylbenzamide as a white solid (12.6 g, 90.7% yield). $^1$H-NMR (300 MHz, DMSO-d$_6$): δ 3.52 (s, 3H), 3.33 (s, 3H).

Example 3. Preparation of 2,5-dibromo-3,4,6-trifluorobenzaldehyde

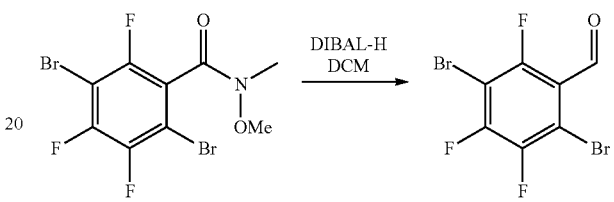

To a solution of 2,5-dibromo-3,4,6-trifluoro-N-methoxy-N-methylbenzamide (12 g, 31.8 mmol, 1.00 equiv.) in dichloromethane (120 mL) was added dropwise a solution of 1 M DIBAL-H (35 mL, 35 mmol, 1.1 equiv.) at −65±5° C. under Nitrogen atmosphere. The reaction mixture was stirred at −65±5° C. for 1.5 hours followed by adding additional solution of 1M DIBAL-H (16 mL, 16 mmol, 0.50 equiv.). After stirring at −65±5° C. for additional 1.5 hours, the mixture was quenched with 10% potassium sodium tartrate aqueous solution (75 mL). The organic layer was separated and concentrated using rotary evaporation. The residue was purified by trituration with heptane to provide 2,5-dibromo-3,4,6-trifluorobenzaldehyde as an off-white solid (8.2 g, 81% yield). $^1$H-NMR (300 MHz, DMSO-d$_6$): δ 10.11 (s, 1H).

Example 4. Preparation of 1-(tert-butyl) 2-methyl 5-bromo-4,6,7-trifluoro-1H-indole-1,2-dicarboxylate

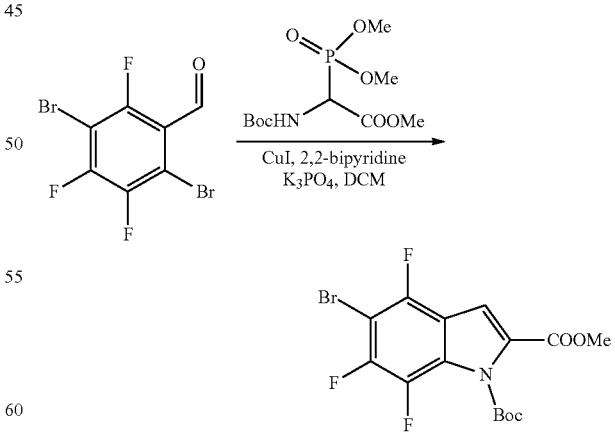

To a flask were added 2,5-dibromo-3,4,6-trifluorobenzaldehyde (6.5 g, 20.4 mmol, 1.00 equiv.), (±)-Boc-α-phosphonoglycine trimethyl ester (6.7 g, 22.5 mmol, 1.10 equiv.), cuprous iodide (1.6 g, 8.4 mmol, 0.40 equiv.), 2,2'-bipyridine (1.31 g, 8.4 mmol, 0.40 equiv.), potassium phosphate tribasic (26 g, 122 mmol, 6.00 equiv.) and dichloromethane (65 mL). The resulting mixture was degassed, flushed with Nitrogen and stirred at ambient temperature for 15 hours. The reaction mixture was quenched with 3 N aqueous hydrochloride acid solution. The organic layer was separated and concentrated. The residue was purified by crystallization from a mixture of methanol and heptane to provide 1-(tert-butyl) 2-methyl 5-bromo-4,6,7-trifluoro-1H-indole-1,2-dicarboxylate as a white solid (7.1 g, 85% yield). $^1$H-NMR (300 MHz, CDCl$_3$): δ 7.25 (s, 1H), 3.96 (s, 3H), 1.67 (s, 9H).

Example 5. Preparation of 1-(tert-butyl) 2-methyl 4,6,7-trifluoro-1H-indole-1,2-dicarboxylate

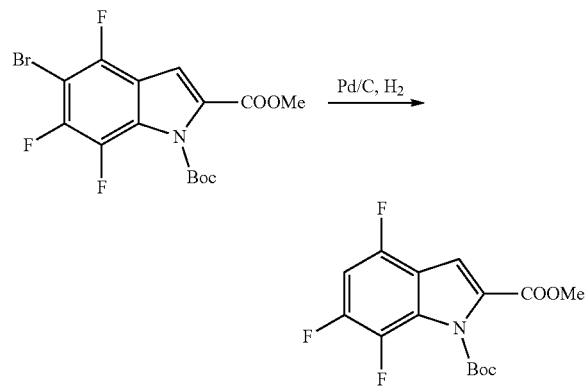

A mixture of 1-(tert-butyl) 2-methyl 5-bromo-4,6,7-trifluoro-1H-indole-1,2-dicarboxylate (6 g, 14.7 mmol, 1.00 equiv.) and 10% palladium on carbon (300 mg, 0.05× by weight) in methanol (30 mL) was stirred under 1 atm of Hydrogen at 20±5° C. for 14 hours. The reaction mixture was filtered to remove catalyst. The collected filtrate was concentrated to provide the desired product 1-(tert-butyl) 2-methyl 4,6,7-trifluoro-1H-indole-1,2-dicarboxylate as a white solid (3.4 g, 86.7% yield). $^1$H-NMR (300 MHz, CDCl$_3$): δ 7.25 (s, 1H), 6.79-6.87 (m, 1H), 3.95 (s, 3H), 1.68 (s, 9H).

Example 6. Preparation of 4,6,7-trifluoro-1H-indole-2-carboxylic acid

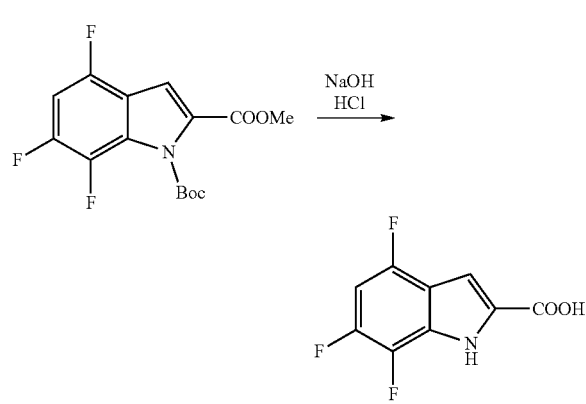

1-(tert-butyl) 2-methyl 4,6,7-trifluoro-1H-indole-1,2-dicarboxylate (3.3 g, 10 mmol, 1.0 equiv.) was added sodium hydroxide (1.0 g, 25 mmol, 2.5 equiv.), water (33 mL) and methyl t-butyl ether (3.3 mL). The reaction mixture was stirred at 60±5° C. for 3 to 6 hours. After the reaction deemed completion, the reaction mixture was cooled to 5±5° C. A 2N hydrochloride acid aqueous solution was added slowly until the pH of the mixture is below 3. The resulting suspension was stirred for 1 hour and filtered. The filter cake was washed with water and dried to provide desired 4,6,7-trifluoro-1H-indole-2-carboxylic acid as an off-white solid (1.7 g, 79.1% yield). $^1$H-NMR (300 MHz, DMSO-d$_6$): δ 13.37 (s, 1H), 12.86 (s, 1H), 7.16 (S, 1H) 7.12 (m, 1H).

Example 7. Preparation of 2,3,5-trifluorobenzoic acid

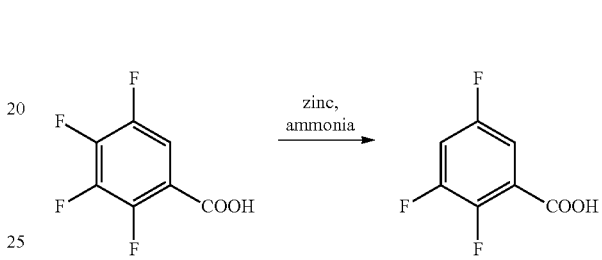

To a flask were added 2,3,4,5-tetrafluorobenzoic acid (100 g, 515.2 mmol), ammonia (300 mL, 3 V) and zinc (101.1 g, 1545.6 mmol, 3 eq.) at 25±5° C. The mixture was stirred at RT for 3 days. The unreacted zinc was removed by filtration. The filtrate was acidified with conc. HCl to pH=1. The mixture was extracted with DCM (2×200 mL). After removal of the solvent by rotary evaporation, the product was obtained as a white solid (88.4 g, 97.5% yield). $^1$H-NMR (300 MHz, CDCl$_3$): δ 7.55-7.49 (s, 1H), 7.17-7.22 (m, 1H).

Example 8. Preparation of tert-butyl (2,3,5-trifluorophenyl)carbamate

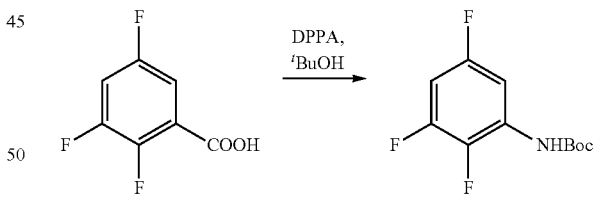

To a flask were added 2,3,5-trifluorobenzoic acid (38 g, 215.7 mmol), tert-butanol (114 mL, 3 V) and Et$_3$N (26.2 g, 258.8 mmol, 1.2 eq.) at 25±5° C. The mixture was gradually heated to 85±5° C., when DPPA (65.3 g, 237.3 mmol) was introduced dropwise. After addition, the mixture was stirred at 85±5° C. for 2 h. After cooling, the mixture was concentrated at 40±5° C. under reduced pressure. The residue was dissolved in 190 mL of MTBE and washed with 5% NaHCO$_3$ (152 mL). The organic layer was separated and concentrated. The residue was purified by column chromatography on silica gel (heptane) to give the product as a white solid (42.7 g, 80.1% yield). $^1$H-NMR (300 MHz, CDCl$_3$): δ 7.71-7.66 (m, 1H), 6.72 (s, 1H), 6.52-6.45 (m, 1H), 1.46 (s, 9H).

Example 9. Preparation of tert-butyl (2,3,5-trifluoro-4-(trimethylsilyl)phenyl)carbamate

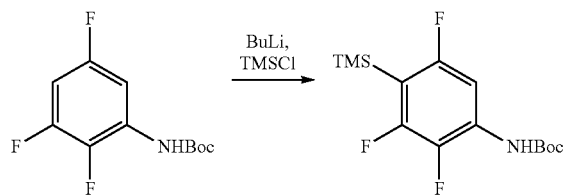 [SMILES: CC(C)(C)OC(=O)Nc1cc(F)cc(F)c1F ; CC(C)(C)OC(=O)Nc1cc(F)c([Si](C)(C)C)c(F)c1F]

To a solution of tert-butyl (2,3,5-trifluorophenyl)carbamate (0.5 g, 2 mmol) in THF was added a solution of BuLi in hexanes (2.5 M, 2 mL, 5 mmol) at −80±5° C. under a N2 atmosphere. After addition, the mixture was stirred at −80±5° C. for 1 h and TMSCl (0.33 mL, 2.6 mmol) was added dropwise via syringe. After stirring at −80±5° C. for 1 h, the mixture was quenched with 5 mL of 10% $NH_4Cl$ and then extracted with MTBE (2×5 mL). The organic layers were combined and concentrated under reduced pressure. The residue was purified by column chromatography on silica gel (EtOAc/heptane=1:20, V/V) to give the product as a colorless oil (396 mg, 62% yield). $^1$H-NMR (300 MHz, $CDCl_3$): δ 7.60-7.65 (m, 1H), 6.77 (s, 1H), 1.53 (s, 9H), 0.35 (s, 9H).

Example 10. Preparation of tert-butyl (4-chloro-2,3,5-trifluorophenyl)carbamate

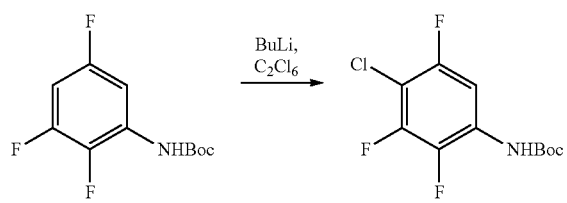 [SMILES: CC(C)(C)OC(=O)Nc1cc(F)cc(F)c1F ; CC(C)(C)OC(=O)Nc1cc(F)c(Cl)c(F)c1F]

To a solution of tert-butyl (2,3,5-trifluoro-4-(trimethylsilyl)phenyl)carbamate (8 g, 32.3 mmol) in THF (56 mL, 7 V) was added dropwise a solution of 2.5 M BuLi (32.2 mL, 80.9 mmol, 2.5 eq.) at −80±5° C. under a $N_2$ atmosphere. The mixture was stirred at −80±5° C. for 1 h and a solution of hexachloroethane (11.5 g, 48.5 mmol, 1.5 eq.) in THF (24 mL, 3 V) was added dropwise at −80±5° C. After stirring at −80±5° C. for 2 h, the mixture was quenched with 40 mL of 5% ammonium chloride (aq.). The mixture was extracted with MTBE (2×40 mL). The organic layers were separated, combined and concentrated. The residue was purified by column chromatography on silica gel (EtOAc/heptane=1:50, V/V) to give the desired product as a white solid (6.8 g, 74.5% yield). $^1$H-NMR (300 MHz, $CDCl_3$): δ 7.94-7.88 (m, 1H), 6.75 (s, 1H), 1.53 (s, 9H).

Example 11. Preparation of tert-butyl (2,3,5-trifluoro-6-formyl-4-(trimethylsilyl)phenyl)carbamate

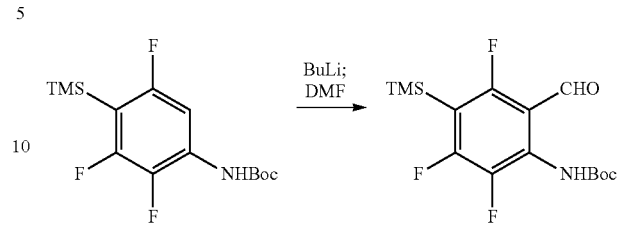

To a solution of F1 (0.3 g, 1.0 mmol) in THF (3 mL, 10 V) was added dropwise a solution of 2.5 M BuLi (2.5 mL, 2.5 mmol, 2.5 eq.) at −80±5° C. under a $N_2$ atmosphere. The mixture was stirred at −80±5° C. for 1 h. DMF was added dropwise at −80±5° C. After stirring at −80±5° C. for 1.5 h, the mixture was quenched with 3 mL of 5% ammonium chloride (aq.). The mixture was extracted with DCM (2×3 mL). The organic layer was separated and concentrated. The residue was purified by column chromatography on silica gel (EtOAc/heptane=1:10, V/V) to give the desired product as an oil (0.1 g, 31.3% yield). $^1$H-NMR (300 MHz, $CDCl_3$): δ 10.24-10.23 (m, 1H), 9.10 (s, 1H), 1.52 (s, 9H), 0.40 (s, 9H).

Example 12. Preparation of tert-butyl (4-chloro-2,3,5-trifluoro-6-formylphenyl)carbamate

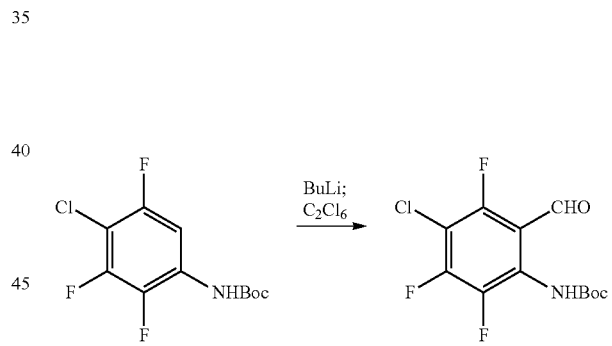

To a solution of tert-butyl (4-chloro-2,3,5-trifluorophenyl)carbamate (3 g, 10.6 mmol) in THF (30 mL, 10 V) was added dropwise a solution of 2.5 M BuLi (10.6 mL, 26.6 mmol, 2.5 eq.) at −80±5° C. under a $N_2$ atmosphere. The mixture was stirred at −80±5° C. for 1 h and DMF (1.9 g, 26.6 mmol, 2.5 eq.) was added dropwise at -80±5° C. After stirring at −80±5° C. for 1.5 h, the mixture was quenched with 15 mL of 5% ammonium chloride (aq.). The mixture was extracted with MTBE (2×15 mL). The organic layers were separated, combined and concentrated. The residue was purified by column chromatography on silica gel (EtOAc/heptane=1:50, V/V) to give the product as a white solid (1.8 g, 54.5% yield). $^1$H-NMR (300 MHz, $CDCl_3$): δ 10.27-10.26 (m, 1H), 8.89 (s, 1H), 1.55-1.52 (m, 9H).

Example 13. Preparation of ethyl 3-(2-((tert-butoxycarbonyl)amino)-3,4,6-trifluoro-5-(trimethylsilyl)phenyl)-2-ethoxyacrylate

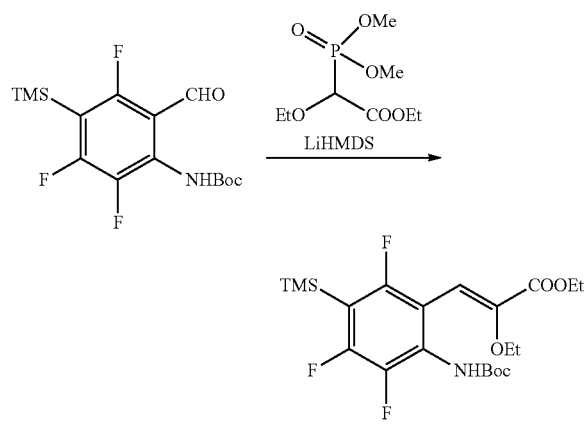

To a solution of ethyl 2-(diethoxyphosphoryl)-2-ethoxyacetate (0.1 g, 0.34 mmol, 1.5 eq) in THF (1 mL, 10V) was added dropwise a solution of 1M LiHMDS (0.4 mL, 0.4 mmol, 1.74 eq.) at 0±5° C. under a N₂ atmosphere. The mixture was stirred at 20±5° C. for 0.5 h and a solution of tert-butyl (2,3,5-trifluoro-6-formyl-4-(trimethylsilyl)phenyl)carbamate (80 mg, 0.23 mmol, 1 eq) in THF (1.6 mL, 20 V) was added dropwise at 0±5° C. After stirring at 0±5° C. for 1 h. the mixture was quenched with 3 mL of 5% aqueous ammonium chloride solution. The mixture was extracted with DCM (2×3 mL). The organic layer was separated and concentrated. The residue was purified by column chromatography on silica gel (EtOAc/heptane=1:20, V/V) to give the desired product as an oil (43 mg, 40.5% yield). ¹H-NMR (300 MHz, CDCl3): δ 7.43 (s, br, 1H), 7.12 (s, 1H), 3.92-4.13 (m, 4H), 1.49 (s, 9H), 1.15-1.28 (m, 6H), 0.38 (s, 9H).

Example 14. Preparation of ethyl 3-(2-((tert-butoxycarbonyl)amino)-5-chloro-3,4,6-trifluorophenyl)-2-ethoxyacrylate

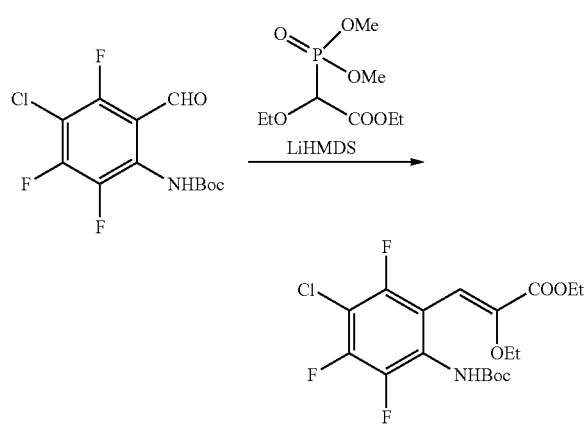

To a solution of ethyl 2-(diethoxyphosphoryl)-2-ethoxyacetate (1.78 g, 5.3 mmol, 1.5 eq) in THF (7.7 mL, 7V) was added dropwise a solution of 1M LiHMDS (5.3 mL, 5.3 mmol, 1.5 eq.) at 0±5° C. under a N₂ atmosphere. The mixture was stirred at 20±5° C. for 0.5 h and a solution of tert-butyl (4-chloro-2,3,5-trifluoro-6-formylphenyl)carbamate (1.1 g, 3.5 mmol, 1 eq) in THF (3.3 mL, 3 V) was introduced dropwise at 0±5° C. After stirring at 0±5° C. for 1 h. the mixture was quenched with 10 mL of 10% aqueous citric acid solution. The mixture was extracted with MTBE (2×10 mL). After removal of the solvent by rotary evaporation, the crude product was obtained as a white solid (0.85 g).

Example 15. Preparation of ethyl 4,6,7-trifluoro-1H-indole-2-carboxylate

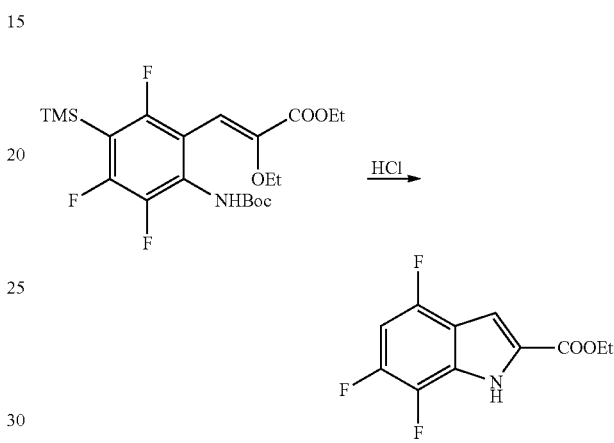

To a flask were added ethyl 3-(2-((tert-butoxycarbonyl)amino)-3,4,6-trifluoro (trimethylsilyl)phenyl)-2-ethoxyacrylate (43 mg, 0.1 mmol) and 4M HCl in EtOH (1.3 mL, 30 V) at 25±5° C. The mixture was gradually heated to 80±5° C. After stirring at 80±5° C. for 6 h, the mixture was concentrated at 40±5° C. under reduced pressure. The mixture was dissolved in 3 mL of DCM and washed with 5% NaHCO₃ solution (2 mL). The organic layer was separated and concentrated. The residue was purified by column chromatography on silica gel (heptane) to give the product as a white solid (20 mg, 88.5% yield). ¹H-NMR (300 MHz, CDCl₃): δ 9.09 (s, 1H), 6.99 (s, 1H), 6.85-6.76 (s, 1H), 4.18-4.11 (m, 2H), 1.28-1.19 (m, 3H).

Example 16. Preparation of ethyl 5-chloro-4,6,7-trifluoro-1H-indole-2-carboxylate

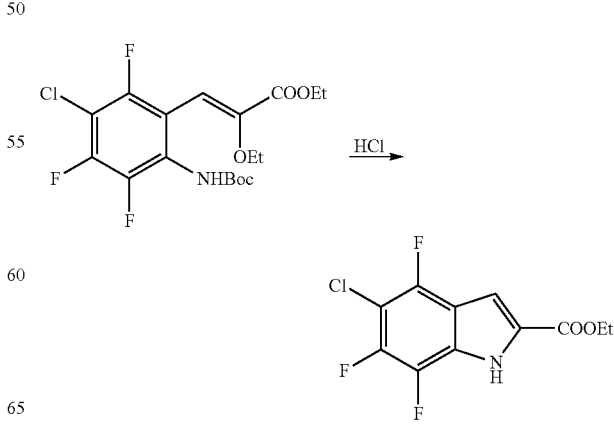

To another flask were added ethyl 3-(2-((tert-butoxycarbonyl)amino)-5-chloro-3,4,6-trifluorophenyl)-2-ethoxyacrylate (0.85 g, 1.9 mmol) and 4M HCl in EtOH (8.5 mL, 10 V.) at 25±5° C. The mixture was heated to 80±5° C. After stirring at 80±5° C. for 6 h, the mixture was concentrated at 40±5° C. under reduced pressure. The residue was dissolved in 10 mL of MTBE and washed with 5% NaHCO3 solution (5 mL). The organic layer was separated and concentrated. The residue was purified by column chromatography on silica gel (EtOAc/heptane=1:5, V/V) to give the desired product as a white solid (0.32 g, 58.2% yield). $^1$H-NMR (300 MHz, CDCl$_3$): δ 9.34 (s, 1H), 6.98 (s, 1H), 4.20-4.13 (m, 2H), 1.31-1.26 (m, 3H).

Example 17. Preparation of ethyl 4,6,7-trifluoro-1H-indole-2-carboxylate

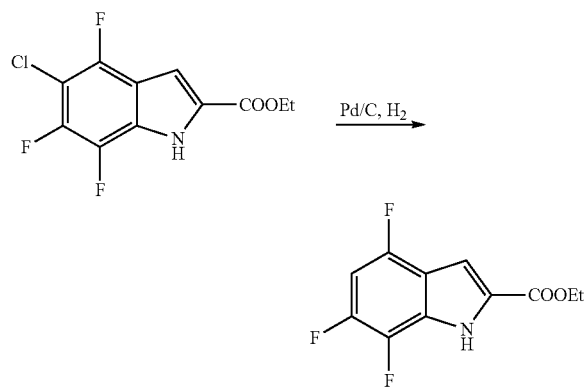

A mixture of L4 (0.32 g, 1.2 mmol) and 10% Pd/C (32 mg, 0.1×) in MeOH (6 mL) was stirred under 1 atm of H$_2$ at 20±5° C. for a week. The catalyst was filtered off and the filtrate was concentrated to give the desired product as a white solid (0.24 g, 85.7% yield). $^1$HNMR (300 MHz, CDCl$_3$): δ 9.09 (s, 1H), 6.94 (s, 1H), 6.76-6.70 (s, 1H), 4.11-4.04 (m, 2H), 1.51-1.47 (m, 3H).

Example 18. Preparation of 4,6,7-trifluoro-1H-indole-2-carboxylic acid

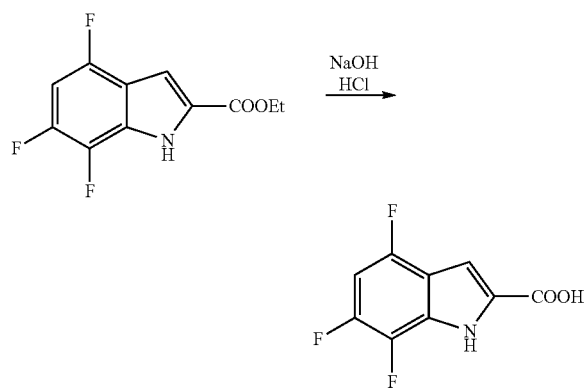

To a flask were added ethyl 4,6,7-trifluoro-1H-indole-2-carboxylate (500 mg, 2 mmol), H$_2$O (2.5 mL, 5 V.), THF (1 mL, 2 V) and NaOH (0.5 g, 12 mmol) at 25±5° C. The mixture was heated to 65±5° C. After stirring at 65±5° C. for 24 h, the mixture was acidified with 3 N HCl aqueous solution and extracted with DCM (2×5 mL). The organic layers were combined and concentrated. The residue was triturated with heptane and toluene to give the desired product as a white solid (360 mg, 81.8% yield). $^1$H-NMR (300 MHz, DMSO-d6): δ 13.48 (s, br, 1H), 12.86 (s, 1H), 7.12-7.21 (m, 2H).

Example 19. Preparation of 2-bromo-3,4,6-trifluoroaniline

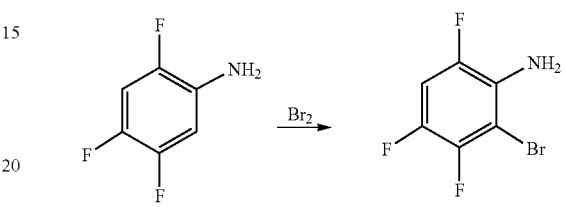

To a solution of 2,4,5-trifluoroaniline (74.5 g, 50.6 mmol) in HOAc (350 mL) was added a solution of bromine (81 g, 50.7 mmol) in HOAc (100 mL) at 10±5° C. After addition, the mixture was stirred at 20±5° C. for 17 h. The precipitated solid was collected by filtration. The solid was dissolved in 150 mL of DCM and treated with 5% Na$_2$CO$_3$ till no more evolution of CO$_2$. 150 mL of 10% of Na$_2$SO$_3$ (aq.) was added and the mixture was stirred for 2 h. The organic layer was separated and concentrated. The residue was dissolved in 50 mL of 4 M HCl in EtOH and then concentrated. The crude salt was recrystallized from 150 mL of HOAc. The pure product was collected by filtration and further freed with 5% Na$_2$CO$_3$ (aqueous solution) to give the free base as an off-white solid (63.5 g, 55.5% yield). $^1$H-NMR (300 MHz, DMSO-d6): δ 7.44 (m, 1H), 5.49 (s, br, 2H).

Example 20. Preparation of 2-bromo-3,4,6-trifluorobenzonitrile

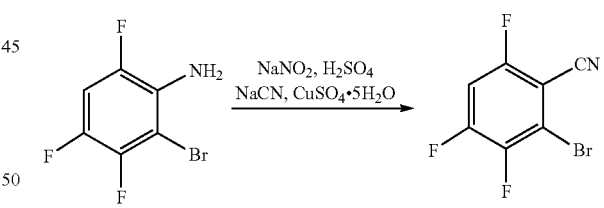

To a solution of 2-bromo-3,4,6-trifluoroaniline (5 g, 22.1 mmol) in H$_2$SO$_4$ (6 N, 30 mL) was added dropwise a solution of NaNO$_2$ (1.68 g, 24.3 mmol) in water (10 mL) at 0±5° C. After stirring at 0±5° C. for 1 h, the diazonium solution was added to another flask containing NaCN (17.7 g, 361 mmol), CuSO$_4$·5H$_2$O (22.6 g, 90.5 mmol), NaHCO$_3$ (32 g, 381 mmol), water (150 mL) and toluene (30 mL) at 50±5° C. over a period of 0.5 h. After stirring for 0.5 h, the mixture was cooled to RT and extracted with EtOAc (2×30 mL). The organic layers were combined and concentrated to give a reddish oil, which was purified by column chromatography on silica gel (EtOAc/heptane, from 1:50 to 1:20, V/V) to give the desired product as a brown solid (1.93 g, 38.6% yield). $^1$H-NMR (300 MHz, DMSO-d6): δ 8.04-8.13 (m, 1H).

Example 21. Preparation of 2-bromo-3,4,6-trifluorobenzaldehyde

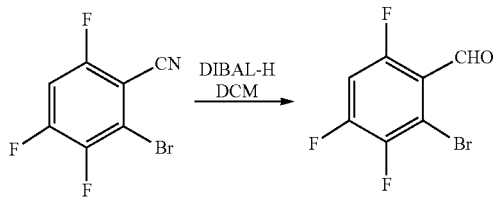 [SMILES: N#Cc1c(F)cc(F)c(F)c1Br ; "DIBAL-HDCM" ; O=Cc1c(F)cc(F)c(F)c1Br]

To a solution of 2-bromo-3,4,6-trifluorobenzonitrile (1.19 g, 5 mmol) in DCM (120 mL, 10 V) was added dropwise a solution of 1 M DIBAL-H (5 mL, 5 mmol, 1.0 eq.) at −40±5° C. under a $N_2$ atmosphere. After addition, the mixture was stirred at −40±5° C. for 3.5 h and complete consumption of the starting material was attained. The mixture was quenched with 10 mL of 10% citric acid (aqueous solution) and extracted with MTBE (2×10 mL). The organic layer was separated and concentrated by rotary evaporation. The residue was purified by TLC (EtOAc/heptane=1:10, V/V) to give the desired product as a yellow oil (322 mg, 27% yield). $^1$H-NMR (300 MHz, CDCl$_3$): δ 10.19 (s, br, 1H), 6.97-7.05 (m, 1H).

Example 22. Preparation of 1-(tert-butyl) 2-methyl 4,6,7-trifluoro-1H-indole-1,2-dicarboxylate

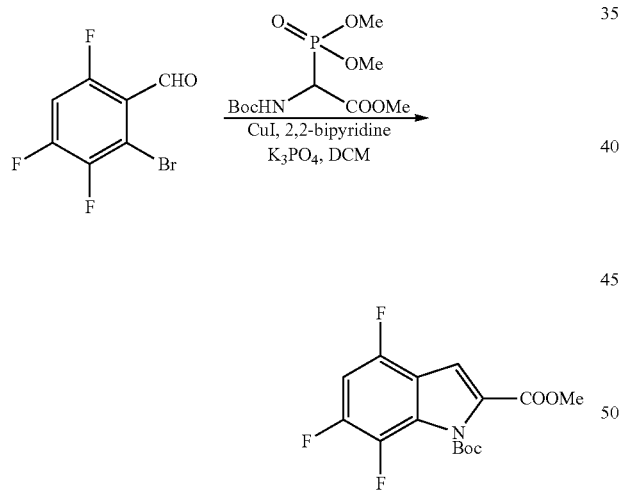

To a flask were added 2-bromo-3,4,6-trifluorobenzaldehyde (50 mg, 0.21 mmol), (±)-Boc-α-phosphonoglycine trimethyl ester (87 mg, 0.29 mmol), CuI (16 mg, 0.084 mmol), 2,2'-bipyridine (13 mg, 0.083 mmol), K$_3$PO$_4$ (266 mg, 125 mmol) and DCM (1 mL). The resulting mixture was degassed, flushed with N$_2$ and then stirred at RT for 16 h. The mixture was quenched with water (10 mL) and extracted with MTBE (2×10 mL). The organic layer was separated and concentrated. The crude oil was purified by TLC (EtOAc/heptane=1:20, V/V) to give a solid (21 mg, 30.5% yield). $^1$H-NMR (300 MHz, CDCl$_3$): δ 7.25 (s, 1H), 6.79-6.87 (m, 1H), 3.95 (s, 3H), 1.68 (s, 9H).

Example 23. Preparation of 4,6,7-trifluoro-1H-indole-2-carboxylic acid

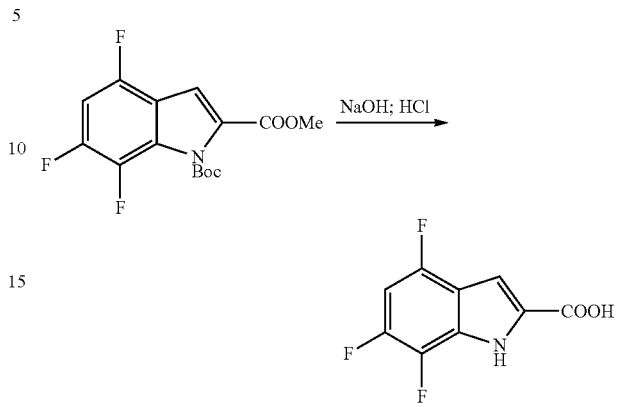

To a solution of 1-(tert-butyl) 2-methyl 4,6,7-trifluoro-1H-indole-1,2-dicarboxylate (500 mg, 1.52 mmol) in 1 mL of THF was added a solution of NaOH (364 mg, 9.1 mmol) in 2.5 mL of water. The resulting mixture was heated at 65±5° C. for 24 h and then concentrated to remove organic volatiles. The residue was acidified with 3 N HCl and then extracted with EtOAc (2×10 mL). The organic layers were combined and concentrated under reduced pressure to give a white solid (272 mg, 83% yield). $^1$H-NMR (300 MHz, DMSO-d6): δ 13.48 (s, br, 1H), 12.86 (s, 1H), 7.12-7.21 (m, 2H).

Example 24. Preparation of (2,5-dibromo-3,4,6-trifluorophenyl)methanol

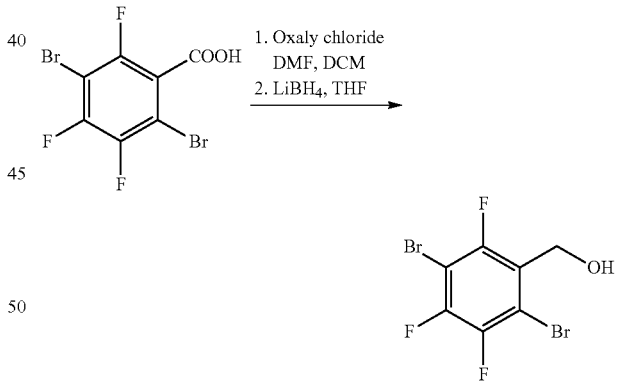

To flask A containing a solution of 2,5-dibromo-3,4,6-trifluorobenzoic acid (30 g, 89.9 mmol) and a drop of DMF in DCM (240 mL, 8 V) was added dropwise a solution of oxalyl chloride (13.7 g, 107.8 mmol, 1.2 eq.) in DCM (60 mL, 2 V). The mixture was stirred at RT for 2 h and IPC showed complete conversion. The benzoyl chloride solution was added dropwise to flask B containing 4 M Lithium borohydride in THF (29 mL, 116.8 mmol, 1.3 eq) at 0±5° C. After addition, the mixture was stirred at 0±5° C. for 1 h and poured slowly to 300 mL of 5% ammonium chloride (aq.) with vigorous stirring. The organic layer was separated and concentrated to give the crude product a brown solid (23 g). $^1$H-NMR (300 MHz, CDCl$_3$): δ 4.87 (s, 2H) 2.12 (s, 1H).

Example 25. Preparation of 2,5-dibromo-3,4,6-trifluorobenzaldehyde

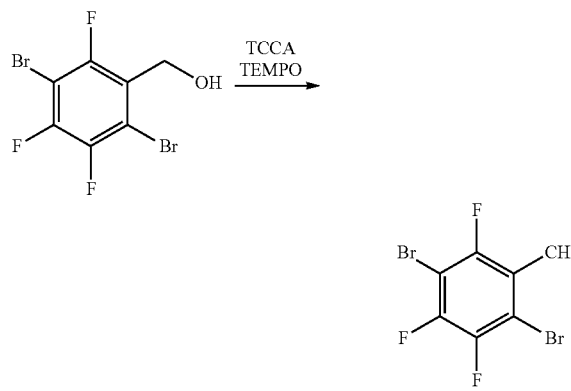

To a mixture of (2,5-dibromo-3,4,6-trifluorophenyl)methanol (23 g, 71.9 mmol) and TEMPO (0.46 g, 2% w/w) in DCM (230 mL, 10V) was added TCCA (11.7 g, 0.8 eq.) in portions at −5±5° C. under a $N_2$ atmosphere. After stirring at −5±5° C. for 30 min, the mixture was quenched with 230 mL of 5% sodium bicarbonate (aq.). The organic layer was separated and washed with 10% citric acid (aq.). After separation, the organic layer was concentrated to give 2,5-dibromo-3,4,6-trifluorobenzaldehyde as a pinkish solid (22.4 g, 80% isolated yield for two steps). $^1$H-NMR (300 MHz, $CDCl_3$): δ 10.18 (s, 1H).

Example 26. Preparation of methyl 2-benzamido-3-(2,5-dibromo-3,4,6-trifluorophenyl)acrylate

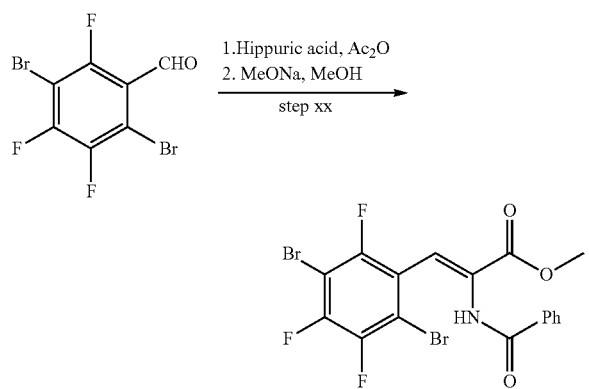

To a flask were added 2,5-dibromo-3,4,6-trifluorobenzaldehyde (5.0 g, 15.7 mmol), hippuric acid (3.4 g, 1.2 eq.), $Ac_2O$ (3.5 g, 2.2 eq.) and toluene (50 mL, 10 V). The resulting mixture was flushed with $N_2$ and heated to 105±5° C. After stirring for 4 h at 105±5° C., the mixture was cooled and concentrated. DCM (50 mL, 10 V) was added to dissolve the residue and MeONa in MeOH (3.4 g, 1.2 eq) was added dropwise at 20±5° C. After stirring for 2 h at 20±5° C., $H_2O$ (50 mL, 10 V) was introduced and two layers were separated. The organic layer was concentrated to give a brown oil (6.5 g, 84.2% isolated yield). There are two double bond isomers.

Isomer 1: $^1$H-NMR (300 MHz, $CDCl_3$): δ 8.67 (s, br, 1H), 8.21 (s, 1H), 7.91 (m, 2H), 7.51-7.64 (s, 3H), 3.75 (s, 3H).

Isomer 2: $^1$H-NMR (300 MHz, $CDCl_3$): δ 8.30 (s, br, 1H), 7.76-7.79 (m, 2H), 7.45-7.57 (m, 3H), 7.23 (s, 1H), 3.98 (s, 3H).

Example 27. Preparation of methyl 1-benzoyl-5-bromo-4,6,7-trifluoro-1H-indole-2-carboxylate

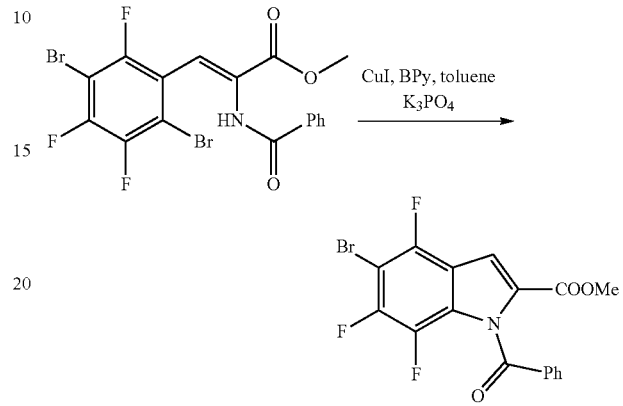

To a dry flask were added methyl 2-benzamido-3-(2,5-dibromo-3,4,6-trifluorophenyl)acrylate (6.5 g, 13.2 mmol), $K_3PO_4$ (5.6 g, 26.5 mmol, 2 eq.), 2,2'-bipyridine (1.2 g, 0.6 eq), CuI (1.5 g, 0.6 eq) and toluene (65 mL, 10 V). The resulting mixture was heated to 105±5° C. under a Na atmosphere. After stirring at 105±5° C. for 16 h, the mixture was cooled to 20±5° C. and filtered. The cake was rinsed with toluene, the filtrate was concentrated to give a brown solid (4.0 g, 73.3% isolated yield). $^1$H-NMR (300 MHz, $CDCl_3$): δ 7.73-7.76 m, 2H), 7.64-7.67 (m, 1H), 7.43-7.51 (m, 3H), 3.76 (s, 3H).

Example 28. Preparation of methyl 4,6,7-trifluoro-1H-indole-2-carboxylate

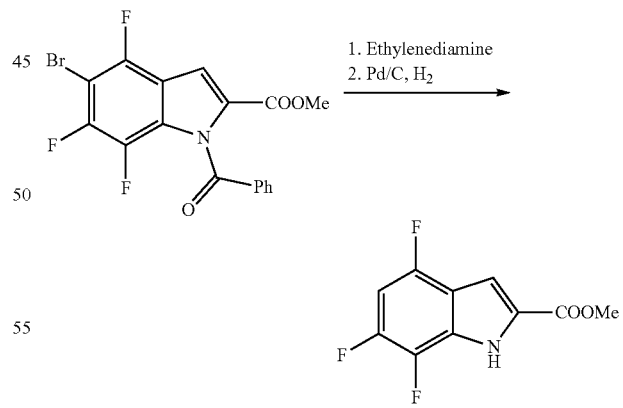

To a solution of methyl 1-benzoyl-5-bromo-4,6,7-trifluoro-1H-indole-2-carboxylate (4.0 g, 9.85 mmol) in DCM (40 mL, 10 V) was added ethylenediamine (1.36 g, 2.3 eq). The resulting mixture was stirred at 20±5° C. for 8 h and MTBE (40 mL, 10 V) was added. After stirring for 1 h, the mixture was filtered and the cake was washed with MTBE. The cake was dissolved in THF (20 mL, 5 V) and hydrogenated over Pd/C (1.0 g, 0.25 w/w) under 1 atm of $H_2$ at RT for 30 h. The catalyst was filtered off and the filtrate was concentrated to give a gray solid (1.5 g, 67.6% isolated yield). ¹H-NMR (300 MHz, DMSO-d6): δ 13.01 (s, br, 1H), 7.22 (s, 1H), 7.11-7.20 (m, 1H), 3.90 (s, 3H).

Example 29. Preparation of 4,6,7-trifluoro-1H-indole-2-carboxylic acid

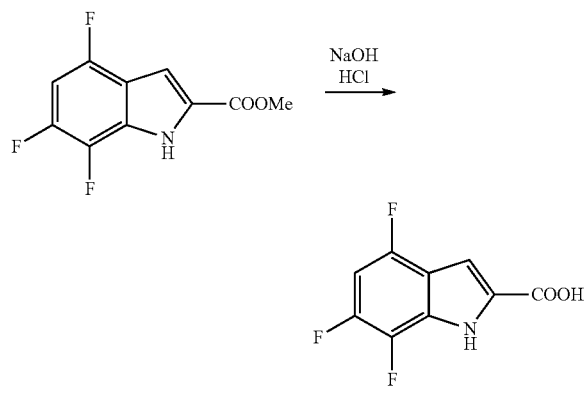

To a solution of methyl 4,6,7-trifluoro-1H-indole-2-carboxylate (1.3 g, 5.7 mmol) in THF (6.5 mL, 5 V) was added a solution of NaOH (1.1 g, 4.8 eq) in H₂O (6.5 mL, 5 V). The mixture was heated at 65±5° C. for 24 h and cooled to RT. The organic layer was separated and discarded. The aqueous phase was further extracted with MTBE (6.5 mL, 5 V) and the extract was discarded. The aqueous layer was acidified with 1 N HCl to pH<3. After stirring at RT for 2 h, the precipitated solid was collected by filtration and dried to give the final compound as a white solid (0.990 g, 81.1% isolated yield). ¹H-NMR (300 MHz, DMSO-d6): δ 13.48 (s, br, 1H), 12.86 (s, 1H), 7.11-7.20 (m, 2H).

Example 30. Preparation of 1-benzyl 2-methyl 5-bromo-4,6,7-trifluoro-1H-indole-1,2-dicarboxylate

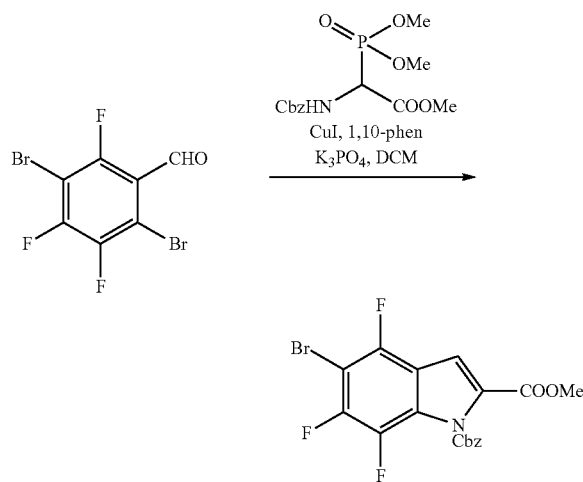

To a flask were added 2,5-dibromo-3,4,6-trifluorobenzaldehyde (1.0 g, 3.14 mmol), (±)-Z-a-phosphonoglycine trimethyl ester (1.15 g, 3.47 mmol, 1.1 eq.), CuI (60 mg, 0.315 mmol, 0.1 eq.), 1,10-phen (57 mg, 0.316 mmol, 0.1 eq.), K₃PO₄ (3.0 g, 14.1 mmol, 4.5 eq.) and DCM (10 mL, 10 V). The resulting mixture was degassed, flushed with Na and stirred at RT for 18 h. The mixture was quenched with 10 mL of 3 N HCl (aqueous solution). The organic layer was separated and concentrated. The crude product (1.91 g) was used directly to the next step. ¹H-NMR (300 MHz, CDCl₃): δ 7.32-7.39 (m, 5H), 5.39 (s, 2H), 3.76 (s, 3H).

Example 31. Preparation of 5-bromo-4,6,7-trifluoro-1H-indole-2-carboxylic acid

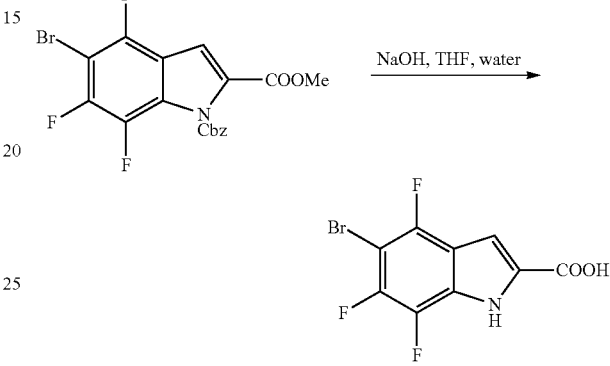

To a solution of NaOH (674 mg, 18.6 mmol) in water (9.5 mL) was added a solution of crude 1-benzyl 2-methyl 5-bromo-4,6,7-trifluoro-1H-indole-1,2-dicarboxylate (1.91 g) in THF (3.8 mL). The mixture was stirred heated at 65±5° C. overnight. The mixture was cooled to RT and extracted with MTBE (2×10 mL). The organic layers were discarded and the aqueous phase was acidified with 3 N HCl (15 mL, aqueous solution) and extracted with MTBE (15 mL). The organic layer was concentrated to give a crude solid. The crude solid was triturated with 4 mL of heptane and 2 mL of toluene under reflux for 1 h. After cooling to RT, the solid (514 mg, 97% purity, 55.8% isolated yield for 2 steps) was collected by filtration. 41-NMR (300 MHz, DMSO-d₆): δ 13.50 (s, br, 1H), 13.09 (s, 1H), 7.21 (s, 1H).

Example 32. Preparation of 4,6,7-trifluoro-1H-indole-2-carboxylic acid

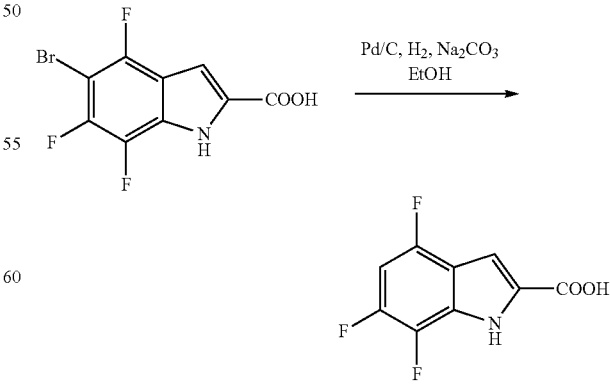

To a flask were added 5-bromo-4,6,7-trifluoro-1H-indole-2-carboxylic acid (470 mg, 1.6 mmol), 10% Pd/C (47 mg, 0.1 W), Na₂CO₃ (340 mg, 3.2 mmol, 2 eq.) and EtOH (4.7 mL, 10 V). The resulting mixture was hydrogenated under 1 atm of H₂ at RT for 42 h and then filtered. The filtrate was concentrated. The residue was treated with 5 mL of 3 N HCl and extracted with EtOAc (2×5 mL). The organic layers were combined and concentrated to give Compound (1) as a white solid (320 mg, 98% purity, 93% isolated yield). ¹H-NMR (300 MHz, DMSO-d6): δ 13.48 (s, br, 1H), 12.86 (s, 1H), 7.12-7.21 (m, 2H).

While this invention has been particularly shown and described with references to preferred embodiments thereof, it will be understood by those skilled in the art that various changes in form and details may be made therein without departing from the scope of the invention encompassed by the appended claims.

What is claimed is:

1. A process for producing Compound (1),

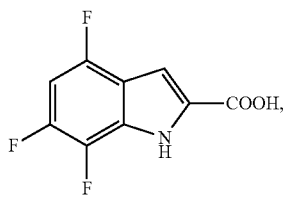

said process comprising the steps of:
(i) reacting Compound (a) with a bromination agent, to produce Compound (b):

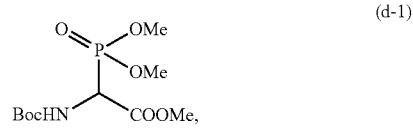

(ii) reacting Compound (b) with N,O-dimethylhydroxylamine HCl, in the presence of an acid activation agent to produce Compound (c):

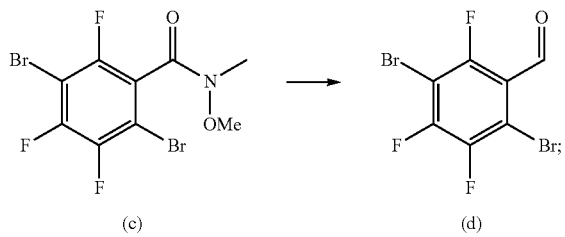 [SMILES: CON(C)C(=O)c1c(F)c(Br)c(F)c(F)c1Br ; O=Cc1c(F)c(Br)c(F)c(F)c1Br]

(iii) reducing Compound (c) with a reducing reagent to produce Compound (d):

(iv) reacting Compound (d) with Compound (d-1)

to produce Compound (e):

(v) reacting Compound (e) with a hydrogen source, to produce Compound (f):

-continued

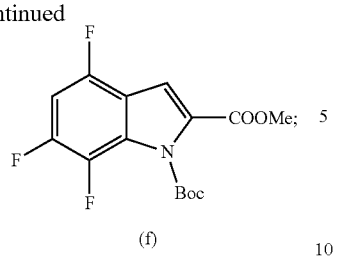

(f)

and (vi) hydrolyzing Compound (f) to produce Compound (1):

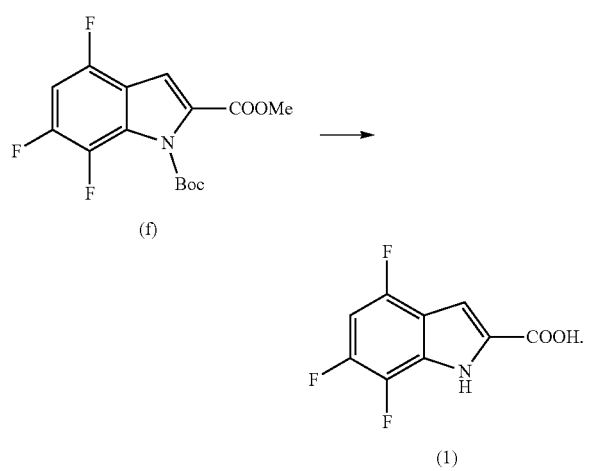

2. The process of claim 1, wherein
in step (i), the bromination reagent is 1,3-dibromo-5,5-dimethylhydantoin;
in step (ii), the chlorination agent is oxalyl chloride;
in step (iii), the reducing reagent is diisobutylaluminium hydride;
in step (iv), the reaction is conducted in the presence of a catalyst selected from the group consisting of cuprous iodide, copper (I) oxide, and [1,1'-Bis(diphenylphosphino) ferrocene] palladium (II) dichloride, and an optional ligand;
in step (v), the reaction is conducted in the presence of a catalyst selected from the group consisting of palladium on carbon, palladium hydroxide on carbon, and Raney nickel; and
in step (vi), the reaction is conducted in the presence of a base to remove the Boc group and methyl ester.

3. The process of claim 1, wherein
in step (i), the reaction is conducted in a solvent, wherein the solvent is sulfuric acid;
in step (ii), the reaction is conducted in the presence of dimethyl formamide as a catalyst;
in step (iii), the reaction is conducted at a temperature from about −70° C. to about −60° C.;
in step (iv), the catalyst is cuprous iodide, the ligand is 2,2'-bipyridine, and the base is potassium phosphate tribasic;
in step (v), the hydrogen source is $H_2$, the catalyst is palladium on carbon (5-10 mol %), and the hydrogen pressure is about 1 atm; and
in step (vi), the reaction is conducted in the presence of sodium hydroxide and the resulting reaction mixture is treated with hydrogen chloride to form Compound (1).

4. A process for producing the Compound (1),

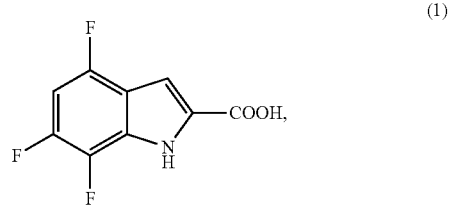 [SMILES: O=C(O)c1cc2c(F)cc(F)c(F)c2[nH]1]

said process comprising the steps of:

(1) reacting Compound (a) with a bromination agent, to produce Compound (b):

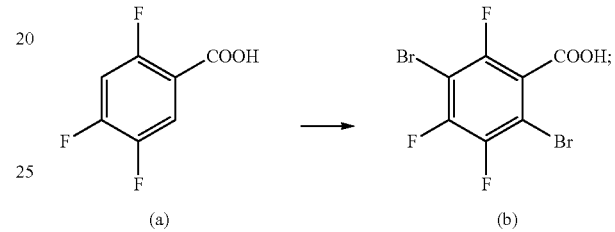

(2) reacting Compound (b) with an acid activation reagent and a reducing agent to produce Compound (c-1):

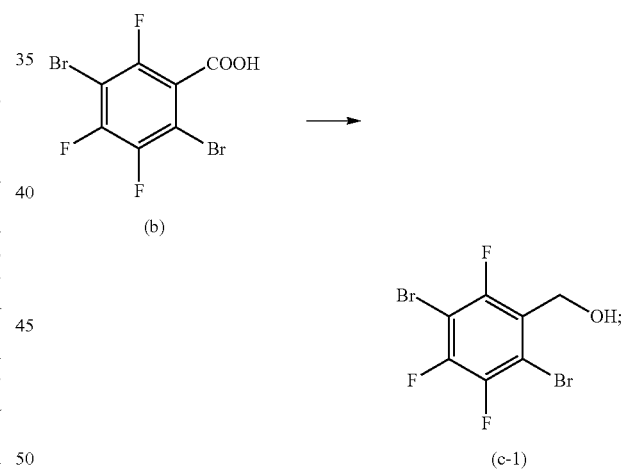

(3) reacting Compound (c-1) with oxidizing agent to produce Compound (d):

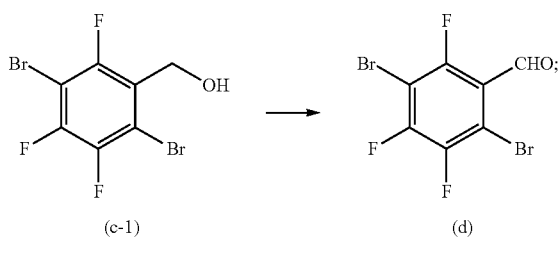 [SMILES: OCc1c(F)c(Br)c(F)c(F)c1Br ; O=Cc1c(F)c(Br)c(F)c(F)c1Br]

(4) reacting Compound (d) with the compound of Formula (D-2)

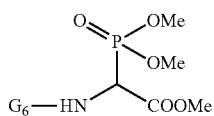
(D-2)

to yield the compound of Formula (E):

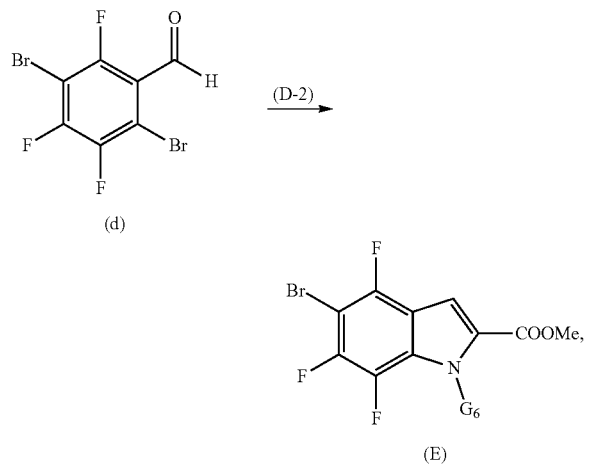

wherein $G_6$ is -Cbz, -Fmoc, -Moz, or -Pnz;

(5) hydrolyzing the compound of Formula (E) to produce Compound (g):

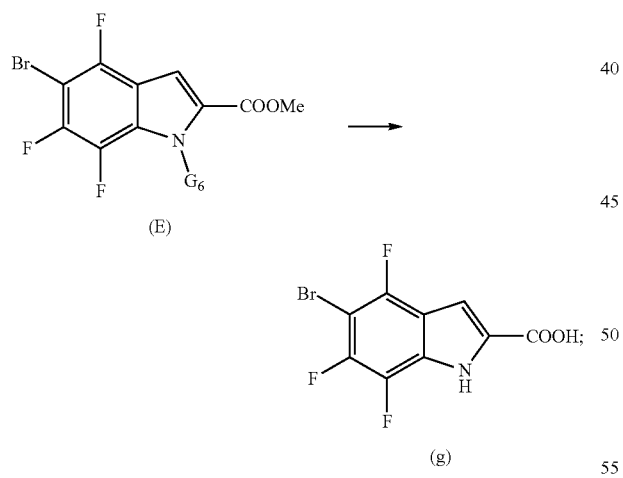

and (6) reacting Compound (g) with a hydrogen source in the presence of a hydrogenation catalyst, to produce Compound (1):

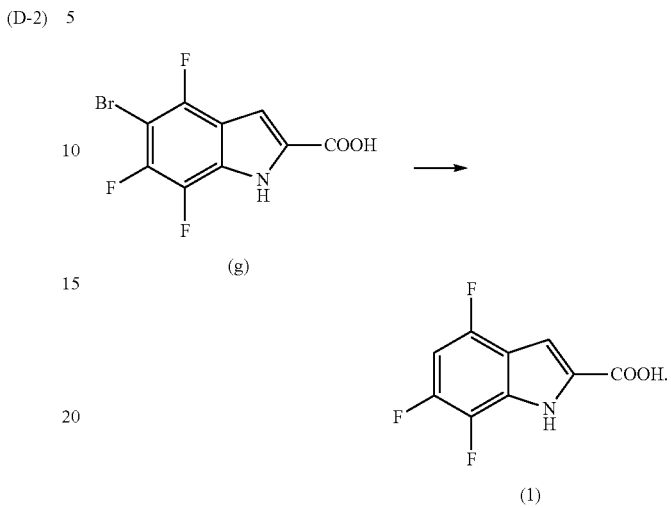

5. The process of claim 4, wherein
in step (1), the bromination reagent is 1,3-dibromo-5,5-dimethylhydantoin;
in step (2), the acid activation agent is oxalyl chloride and the reducing agent is lithium borohydride;
in step (3), the oxidizing agent is trichloroisocyanuric acid with TEMPO;
in step (4), $G_6$ is -Cbz, and the reaction is conducted in the presence of cuprous iodide as a catalyst;
in step (5), the reaction is conducted in the presence of sodium hydroxide as a base; and
in step (6), the reaction is conducted in the presence of palladium on carbon as a catalyst.

6. The method of claim 2, wherein in step (vi), the base is sodium hydroxide, potassium hydroxide, lithium hydroxide, or a mixture of two or more thereof.

7. The process of claim 2, wherein
in step (i), the reaction is conducted in a solvent, wherein the solvent is sulfuric acid;
in step (ii), the reaction is conducted in the presence of dimethyl formamide as a catalyst;
in step (iii), the reaction is conducted at a temperature from about −70 ° C. to about −60 ° C.;
in step (iv), the catalyst is cuprous iodide, the ligand is 2,2'-bipyridine, and the base is potassium phosphate tribasic;
in step (v), the hydrogen source is $H_2$, the catalyst is palladium on carbon (5-10 mol%), and the hydrogen pressure is about 1 atm; and
in step (vi), the reaction is conducted in the presence of sodium hydroxide and the resulting reaction mixture is treated with hydrogen chloride to form Compound (1).

* * * * *